US007177458B1

(12) United States Patent
Savareigo et al.

(10) Patent No.: US 7,177,458 B1
(45) Date of Patent: Feb. 13, 2007

(54) REDUCTION OF FALSE ALARMS IN PCB INSPECTION

(75) Inventors: Nissim Savareigo, Ashdod (IL); Dan Shalom, Rishon Lezion (IL); Nur Arad, Tel Aviv (IL)

(73) Assignee: Orbotech Ltd. (IL)

( * ) Notice: Subject to any disclaimer, the term of this patent is extended or adjusted under 35 U.S.C. 154(b) by 276 days.

(21) Appl. No.: 10/363,982

(22) PCT Filed: Sep. 10, 2000

(86) PCT No.: PCT/IL00/00552

§ 371 (c)(1),
(2), (4) Date: Nov. 12, 2003

(87) PCT Pub. No.: WO02/21105

PCT Pub. Date: Mar. 14, 2002

(51) Int. Cl.
*G06K 9/00* (2006.01)
*H04N 9/47* (2006.01)
*G01B 5/28* (2006.01)
*G01N 21/88* (2006.01)

(52) U.S. Cl. .................. 382/145; 348/126; 702/35; 250/559.45

(58) Field of Classification Search ............... 382/145; 348/126; 702/35; 250/559.45
See application file for complete search history.

(56) References Cited

U.S. PATENT DOCUMENTS

| 4,628,531 | A | * | 12/1986 | Okamoto et al. ........... 382/144 |
| 4,758,888 | A | | 7/1988 | Lapidot |
| 5,146,509 | A | | 9/1992 | Hara et al. |
| 5,204,910 | A | | 4/1993 | Lebeau |
| 5,586,058 | A | * | 12/1996 | Aloni et al. .................. 702/35 |
| 5,619,429 | A | | 4/1997 | Aloni et al. |
| 5,774,572 | A | | 6/1998 | Caspi |
| 5,774,573 | A | * | 6/1998 | Caspi et al. ................ 382/141 |
| 6,360,005 | B1 | | 3/2002 | Aloni et al. |
| 6,850,636 | B1 | * | 2/2005 | Yabe .......................... 382/141 |

FOREIGN PATENT DOCUMENTS

| EP | 0594146 | 4/1994 |
| WO | WO 99/66314 | 12/1999 |
| WO | WO 00/11454 | 3/2000 |
| WO | WO 00/19372 | 4/2000 |
| WO | WO 01/07893 | 2/2001 |

OTHER PUBLICATIONS

Brochure: Inspire 9060—Automated AOI System, Orbotech Ltd., Israel, Jan. 2003.
M. deBerg, M. van Kreveld, M. Uvermars and V. Schwarzkopf, *Computational Geometry*, Springer 1997.
D. Marr, *Vision*, Freeman & Co., New York, 1982.
J. D. Foley et. al., *Computer Graphics: Principles and Practice*, Addison-Wesley, 1990.

* cited by examiner

*Primary Examiner*—Joseph Mancuso
*Assistant Examiner*—Kathleen Yuan
(74) *Attorney, Agent, or Firm*—Sughrue Mion, PLLC

(57) ABSTRACT

A method for automatically optically inspecting an electrical circuit (12), comprising: acquiring at least one optical image of an electrical circuit (12); generating at least one first inspection image from the at least one image and determining regions of candidate defects (236) therefrom; generating at least one additional inspection image for regions surrounding candidate defects (236), said at least one additional inspection image at least partially including optical information not included in the at least one first inspection image; and determining whether the candidate defect (236) is a specious defect by inspecting the at least one additional inspection image.

29 Claims, 17 Drawing Sheets

FIG.3

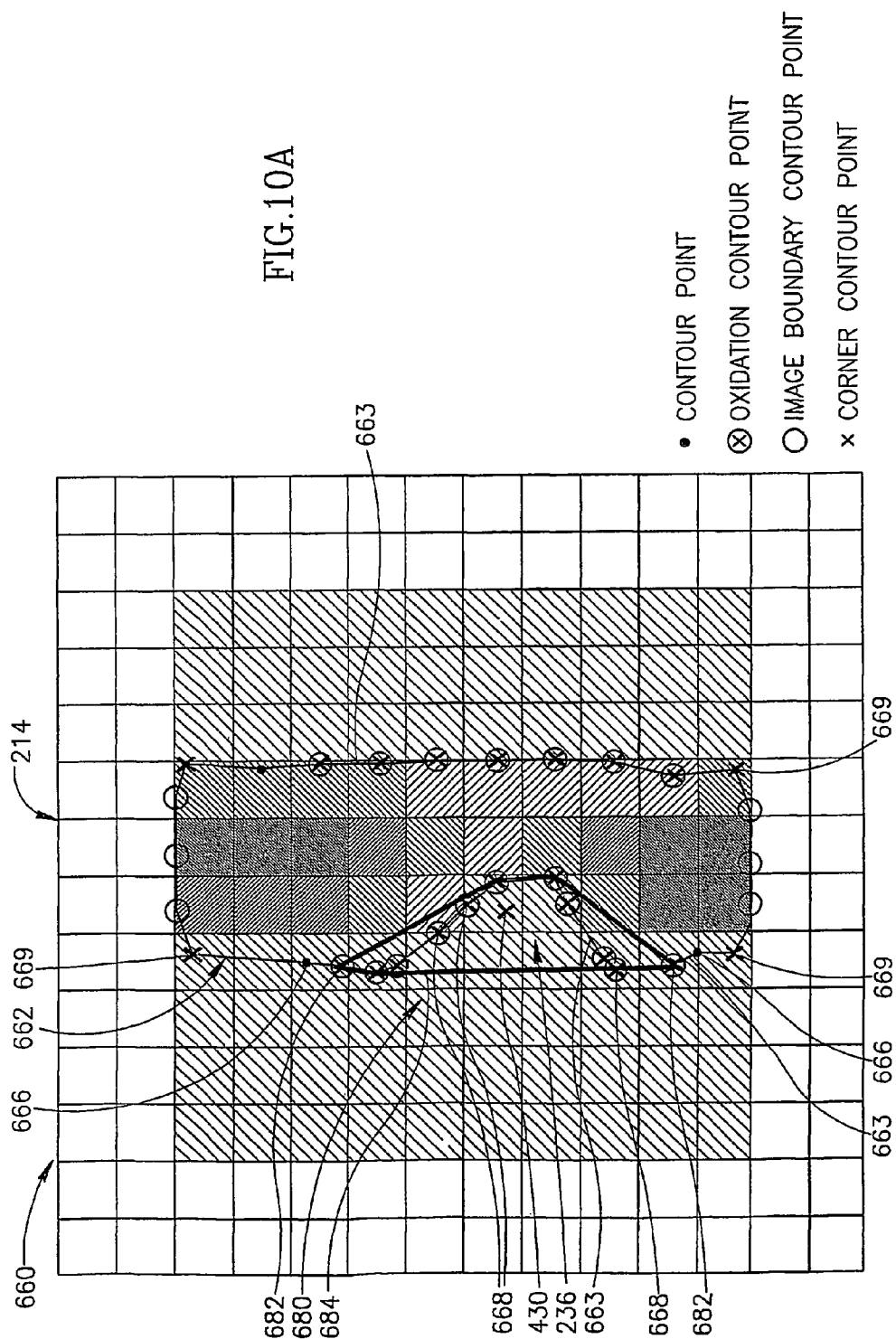

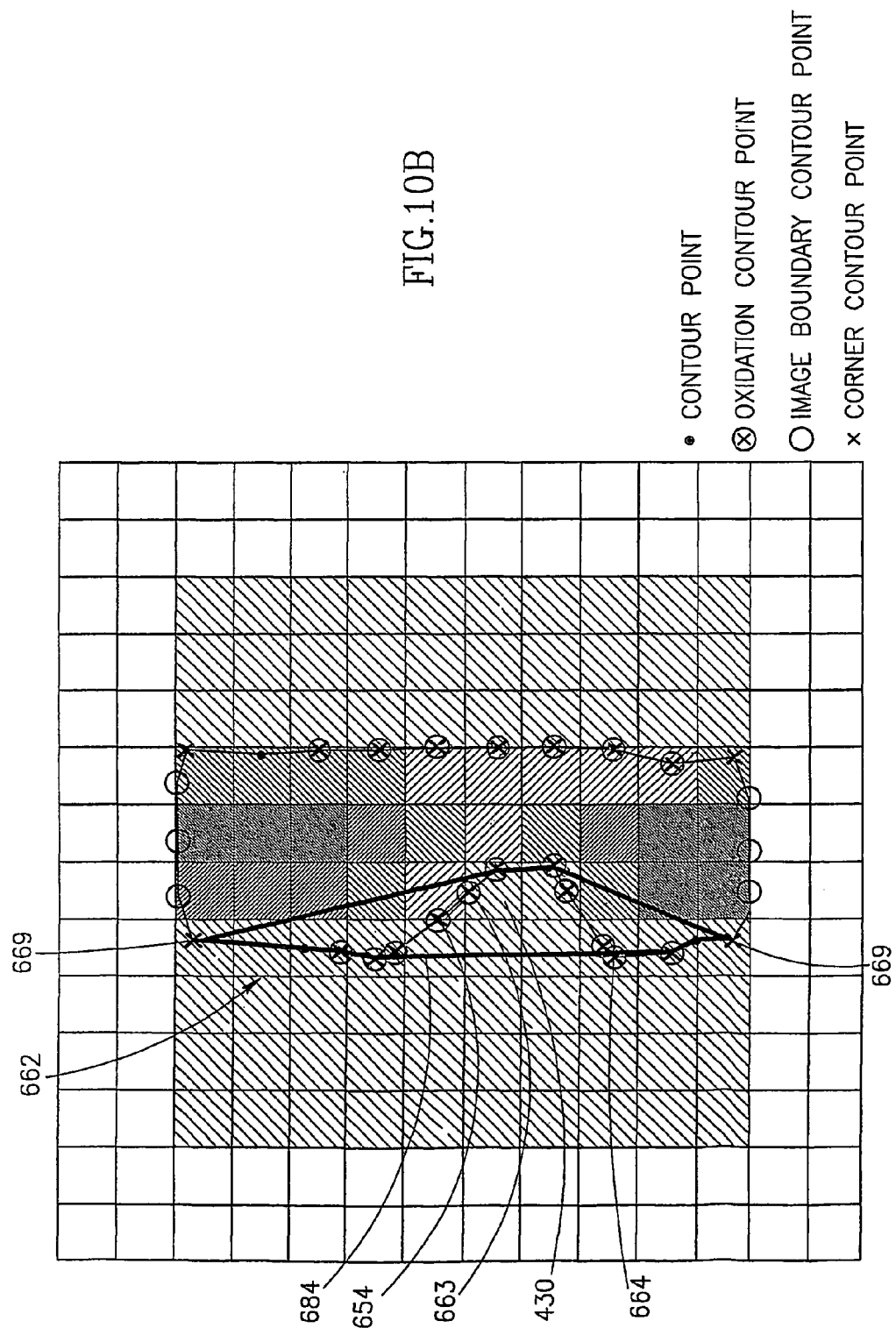

REDUCTION OF FALSE ALARMS IN PCB INSPECTION

FIELD OF THE INVENTION

The present invention relates to methods for the automatic optical inspection of geometrically patterned objects, such as electrical circuits on printed circuit boards (PCBs), and more particularly to methods for reducing false alarms during the inspection thereof.

BACKGROUND OF THE INVENTION

Machine vision based automated inspection systems are widely used to analyze geometric patterns on objects. Typical applications for such systems include the inspection of electrical circuits on printed circuit boards ("PCBs"), flat panel displays, ball grid array substrates, semiconductor chips, reticules, electronic components assembled on PCBs, and the like.

Optical inspection of PCBs, which have metalized conductor portions and unmetalized substrate portions, is performed by: (i) illuminating a portion of a surface of the PCB, (ii) acquiring an image of the illuminated surface portion, and (iii) analyzing brightness over the surface to define conductors in the image. Defects in the PCB are determined by analyzing the image with respect to a reference image and a with respect to a set of standards or rules to determine deviations from the reference and whether the conductors meet certain rules.

Among prior art publications which describe such methods are U.S. Pat. Nos. 4,758,888, 5,586,058, 5,619,429, 5,774,572, and 5,774,573, the disclosures of which are incorporated by reference.

In one conventional method of PCB inspection, employed in various automated optical inspection systems sold by Orbotech Ltd. of Yavne, Israel, a PCB is illuminated with a polychromatic light source and a gray level image of the PCB is acquired at an optical resolution. In the gray level image, pixels are categorized into one of three populations according to brightness: substrate, conductor and regions of intermediate brightness which typically comprise edges between substrate and conductor. The precise location of edges between conductor and substrate are determined to a sub-pixel accuracy and edges that are located in regions of substrate or conductor are discarded. The remaining edges are used to produce a binary representation of the PCB having a resolution which is greater than the optical resolution. The binary image is analyzed to determine defects in the shape of conductors in the electrical circuit.

U.S. Pat. Nos. 5,586,058 and 5,619,429 describe and show an inspection system for inspecting patterned objects such as semiconductor wafers and reticules including a hardware based fine defect inspection pipeline operative to inspect a binary image of the object and a hardware based ultra fine defect inspection pipeline operating substantially in parallel to the fine defect inspection pipeline and operative to inspect a gray level image of the object. The system additionally includes a software based post-processor which is operative to receive real time recorded representations of locations of the inspected object along with binary or gray level reference information. The representations are derived from the same images employed by the fine and ultra-fine inspection pipelines, and are reanalyzed to filter false alarms and to categorize the defects.

One problem typically encountered in automated optical inspection of PCBs occurs when conductor portions on the PCB are oxidized. Oxidation is often merely a superficial blemish that does not affect PCB functionality and as such should not result in the determination of the oxidized region as being defective. However, oxidized conductors typically have a brightness value that is different from the brightness value for non-oxidized metal. Typically the brightness value for oxidation in a red monochrome image for a PCB is intermediate of the respective values of non-oxidized metal and substrate, such that conventional gray level processing does not effectively identify and handle oxidation. Consequently, oxidized portions may be speciously classified as being substrate, even though it is desirable to classify the oxidized portion as being a metalized portion.

As a result, in conventional image inspection methods, conductor portions in the vicinity of oxidization may fail to meet predetermined rules, thus resulting in a specious detection of a defect. For example, metalized portions in the vicinity of oxidation may be speciously classified as having undesired pinholes or as failing to obtain a minimum line width. This problem is particularly prevalent adjacent to border regions between metalized portions and substrate which typically have brightness values that are intermediate of conductor and substrate.

In the PCT Publication application, WO 00/11454, entitled "Inspection of Printed Circuit Boards Using Color", the disclosure of which is incorporated herein by reference, color image processing is used to identify oxidation on PCB conductors. Oxidation is identified by characteristic colors that are different from both non-oxidized metal and substrate. The color processing typically is applied as part of a gray level processing pipeline which is supplemental to binary image processing. Pixels that have a color which is characteristic of oxide are classified as such, and are then treated as if they are unoxidized metal.

SUMMARY OF THE INVENTION

The present invention seeks to provide improved apparatus and methods operative to reduce false alarms that occur during the optical inspection of printed circuit boards.

A general aspect of some embodiments of the present invention relates to a method of image processing in which candidate defects are identified in a first image processing operation that includes binary image processing. Snapshot images of neighborhoods surrounding candidate defects are processed in a second processing operation operative to classify candidate defects and to distinguish between real defects and specious defects. The snapshots may be polychromatic or color images of pixel neighborhoods surrounding candidate defects, and both the binary image and the snapshot image are derived from the same image inputs.

A general aspect of some embodiments of the present invention relates to a method of image processing for determining defects in electrical circuits, comprising a first image processing operation in which a reduced data image, for example a binary or gray monochrome image of an electrical circuit, is analyzed to determine real defects and candidate defects and, in a second image processing stage, a robust image of a region surrounding candidate defects, which contains optical information not included in the reduced data images, is processed to determine real defects and specious defects.

A general aspect of some embodiments of the present invention relates to a method for verifying defects in an electrical circuit wherein an image of the electrical circuit is acquired and analyzed. A representation of features in the image is prepared and then modified according to a rule. The modified representation is processed to determine the presence of defects in the electrical circuit. For example, a representation of contours denoting edges between metal and substrate is prepared, and then modified. If oxidation is found in the vicinity of a modified edge, then the modified representation may be analyzed to determine the presence of defects.

A general aspect of some embodiments of the present invention relates to a method for verifying defects in a patterned object such as an electrical circuit. An image of the electrical circuit is acquired and inspected. Pixels in the image are processed to define contours that represent an approximation of the location of edges between substrate and conductor. Points along the contours are processed to determine if they are oxidized. In conductors in which some of points along the contours are determined to be oxidized, the contour in the vicinity of contour points which are oxidized is revised. The revised contour representation is processed to determine whether a real or specious defect is present in the vicinity of the oxidation.

Alternatively, in accordance with a general aspect of some embodiments of the present invention, contours in a contour representation of an electrical circuit, in which contours represent the approximate location of an edge between metal conductor and substrate, are revised for all regions extending between corners in the contour representation. The region surrounding a revised contour is examined for oxidation. If oxidation is present, the revised contour representation is then analyzed for defects.

In an embodiment of the present invention, an image of a PCB comprising a substrate and metalized conductors is acquired (the "source image"), and a binary image is generated therefrom. The binary image is analyzed to determine the presence of candidate defects. When a metalized conductor on the PCB is determined to have a candidate defect thereon, a neighborhood surrounding the candidate defect, hereinafter referred to as a "test neighborhood", is defined in the source image of the PCB. The test neighborhood is chosen to be large enough so that it includes a sufficient portion of the conductor in which the candidate defect is located to enable the shape of the conductor in the vicinity of the candidate defect to be defined. For example, if the candidate defect is a line width violation, for example the conductor is not sufficiently wide at a particular location, the size of the test neighborhood is chosen to be sufficiently large so that it encompasses an image of contours representing at least both geometrically opposite edges of the conductor in the vicinity of the candidate defect. If the defect is a pad violation, namely that a PCB pad is too small, or otherwise improperly shaped, the size of the test neighborhood is chosen to be sufficiently large so that it encompasses contours that represent substantially the entire pad suspected as being defective.

In an embodiment of the present invention, pixels in the test neighborhood are processed to define contour lines that represent the estimated location of edges between substrate and conductor. Preferably, the location of contour lines is approximated to a sub-pixel accuracy, substantially as described in U.S. Pat. Nos. 5,774,572 and 5,774,573.

According to an aspect of some embodiments of the present invention, images of conductors that extend to the border of a test neighborhood image are truncated a short distance from the image boundary. As a result, a contour which defines an edge between substrate and metalized conductor in test neighborhoods is formed to be a single closed contour line such that the conductor in a test neighborhood appears as if it is an "island" of conducting material having a shape defined by an enclosed contour line. Preferably, the source image of the PCB is a color image and color values of pixels along a contour line are used to determine if points on the contour line are adjacent to oxidized regions of conductor.

According to an aspect of some embodiments of the present invention, a point on a contour line is identified as an oxidation contour point in response to a function of the gradients of reflective light intensity in predetermined light spectra. For example, in electrical circuits on PCBs, oxidation is characterized by a weak gradient, generally for all channels, and high intensity values for red light relative to green and blue light. Thus, in accordance with an embodiment of the present invention, boundaries between oxidized portions of conductor and non-oxidized portions of conductor substrate are determined from a spatial derivative of the intensity of red, green and blue light.

In accordance with an aspect of some embodiments of the present invention, a point is determined to be an oxidation boundary point if the point is located in or near to a region determined to be a region of oxidized conductor. Preferably, regions of a PCB are determined to be oxidized conductor, using methods described in the above referenced application WO 00/11454.

In accordance an aspect of an embodiment of the invention, a multi-pipeline image processor for processing images of electrical circuits is provided. In a first pipeline, a binary image of the circuit is processed to determine defects. In a second pipeline, a gray level monochrome image is processed to determine the presence of defects. Defects are classified as being at least one of real defects and candidate defects. Enhanced optical data image of regions surrounding candidate defects are further processed in a software image processing pipeline. Preferably, the candidate defects are certain types of defects detected in the binary map image processing operations which can be classified as being real or specious based on analysis of a robust optical data image that includes optical data that is not present in either the binary or gray level monochrome image.

There is thus provided, in accordance with an embodiment of the invention, a method for automatically optically inspecting an electrical circuit, comprising:

acquiring at least one optical image of an electrical circuit;

generating at least one first inspection image from the at least one image and determining regions of candidate defects therefrom;

generating at least one additional inspection image for regions surrounding candidate defects, said at least one additional inspection image at least partially including optical information not included in the at least one first inspection image; and determining whether the candidate defect is a specious defect by inspecting the at least one additional inspection image.

In an embodiment of the invention, acquiring includes acquiring a polychromatic image of the electrical circuit. Optionally, the polychromatic image comprises a red, a green and a blue component. Optionally, the additional inspection image comprises each of the red, green and blue components acquired in the polychromatic image.

In an embodiment of the invention, the at least one first inspection image includes a binary representation of the electrical circuit. Optionally, the binary representation is derived only from a red color component of the acquired image.

In an embodiment of the invention, the at least one first inspection image includes a monochromatic gray level representation of the electrical circuit. Optionally the monochromatic gray level representation is derived only from a red color component of the acquired image.

In an embodiment of the invention, the first inspection image and the additional inspection image are derived from the same optical image.

Optionally, the candidate defects and/or the actual defects are determined automatically.

There is further provided, in accordance with a preferred embodiment of the invention, a method of inspecting an electrical circuit, comprising:

providing a binary representation of an electrical circuit;

determining the presence of candidate defects in the electrical circuit at least in part from analyzing the first binary representation;

providing a non-binary image of a region surrounding a candidate defect; and determining the presence of an actual defect in the circuit from analyzing the non-binary image.

Optionally, the binary representation covers a larger extent of the circuit than the non-binary image.

In an embodiment of the invention, determining real defects comprises:

providing a non-binary image in a region surrounding candidate defects determined from the binary image; and processing the non-binary image to verify the presence of the real defect.

Optionally, the method includes providing a gray level monochrome representation of the circuit, and determining candidate defects in the electrical circuit at least in part by analyzing both the binary representation and the gray level monochrome representation. Optionally, the method includes identifying real defects from analyzing the binary representation and the gray level monochrome representation.

In an embodiment of the invention, where defects determined utilizing said binary image include actual defects and wherein said actual defects include one or more of: missing features in an electrical circuit, misplaced features in an electrical circuit, extraneous features in an electrical circuit, pinholes and scratches.

Optionally, the binary image is prepared to a resolution which is finer than an optical resolution of an optical image from which it is derived.

In an embodiment of the invention, where candidate defects comprise suspected shape aberration in a metal conductor in the electrical circuit. In an embodiment of the invention, in an optical image of the electrical circuit metalized portions in the electrical circuit have a first optical characteristic, non-metalized portions have a second optical characteristic, and regions of suspected shape aberration have a third optical characteristic which is different from the optical characteristics of the metalized portions and the non-metalized portions. Optionally, the optical characteristic comprises intensity of reflectance and/or color.

Optionally, providing a binary image comprises providing the binary image from a single channel of a multichannel polychromatic image of the electrical circuit. Optionally, the non-binary image is a polychromatic image of the electrical circuit.

There is further provided, in accordance with an embodiment of the invention, a method of determining defects in electrical circuits, comprising:

acquiring an optical image of an electrical circuit;

generating a representation of the electrical circuit from the image;

analyzing at least part of the representation at a region near a candidate to detect an attribute of the electrical circuit;

revising the representation in response to a detected attribute of the electrical circuit;

processing the revised image to determine the presence of a real defect.

In an embodiment of the invention, the representation is a representation of contours in the electrical circuit. In an exemplary embodiment, the contours are representative of putative edges between metalized portions and substrate portions in the electrical circuit.

In an embodiment of the invention, revising includes evaluating a region in the representation to determine whether it is a metal and revising the contours if metal is detected. In an embodiment of the invention, the metal is oxidized or non-oxidized metal. Optionally, the metal is copper.

In an embodiment of the invention, evaluating includes analyzing a monochromatic image of the region. Alternatively or additionally, in an embodiment of the invention, evaluating includes analyzing a polychromatic image of the region.

In an embodiment of the invention, revising includes calculating a directed convex hull for a section of the contours, and replacing the section with the directed convex hull. Alternatively or additionally, in an embodiment of the invention, revising includes locating points representing corners in a contour located near the candidate defect. Optionally, the directed convex hull extends between corner contour points.

In an embodiment of the invention, revising includes detecting contour points that are situated on oxidized conductors. Optionally, revising includes identifying at least three contiguous oxidized contour points. Optionally, revising includes identifying from among the at least three contiguous oxidized contour points, at least two oxidized contour points each of which is bounded by a contour point that is not oxidized. Alternatively or additionally revising includes identifying from among the at least three contiguous oxidized contour points, at least one oxidized contour point that is also a corner. Optionally, revising includes identifying from among the at least three contiguous oxidized contour points an additional contour point that is bounded by a contour point that is not oxidized.

In an embodiment of the invention, revising includes calculating a directed convex hull between any pair of: oxidized contour points which are bounded by a combination of contour points that are not oxidized and oxidized contour points that are a corner.

In an embodiment of the invention, the attribute comprises an optical attribute characteristic of an oxide.

In an embodiment of the invention, the attribute is an optical attribute comprising a level of reflective intensity in at least two spectral ranges. Optionally, the attribute is an optical attribute comprising a level of reflective intensity in at least three spectral ranges. Optionally, the spectral ranges comprise at least two of red, green and blue.

In embodiments of the invention, processing is performed in response to the detection of metal and/or oxide in the vicinity of the candidate defect. Optionally, the detection of an oxide is performed on contour points located along a putative border between metal conductor and substrate. Alternatively or additionally, the detection of an oxide is performed on the values obtained by pixels for regions in the electrical circuit that are located near the candidate defect.

In an embodiment of the invention, revising includes revising a putative contour to include a directed convex hull.

Optionally, revising includes measuring the distance between putative contours, wherein at least part of the putative contours includes the directed convex hull.

There is further provided, in accordance with an embodiment of the invention, apparatus for automatically optically inspecting electrical circuits, comprising:

at least one optical sensor operative to acquire an image of an electrical circuit;

a first image processor operative to generate a first representation of the electrical circuit from the image and to analyze said first representation to determine therefrom suspected defects in the electrical circuit;

a snapshot generator operative to receive images from the at least one sensor, and reports of suspected defects from the first image processor, and to generate neighborhood images of regions surrounding suspected defects; and an image post processor operative to analyze the neighborhood images and to determine therefrom the presence of real defects.

In an embodiment of the invention, the first image processor generates a first representation which is a binary representation of the electrical circuit. Optionally, the optical sensor has an optical resolution and the binary representation of the electrical circuit is generated a resolution that is finer than the optical resolution. Optionally, when suspected defects are candidate defects and real defects, and the image post processor is operative to analyze neighborhood images for candidate defects. Optionally, the apparatus comprises a gray level image processor, and at least some anomalies detected by the gray level image processor are real defects and at least some anomalies detected by the binary image processor are candidate defects.

Optionally, the neighborhood images are polychromatic images, optionally, color images.

There is further provided, in accordance with an embodiment of the invention, a method for generating a representation of an electrical circuit comprising:

acquiring an image of an electrical circuit including a multiplicity of conductors, said conductors having at least a first distinguishable optical attribute at a first part thereof, and a second distinguishable optical attribute at a second part thereof, and a substrate having a third distinguishable optical attribute, wherein at least some of the second part of the conductors is located between the first part and the substrate; and computer processing the image to produce a representation of the electrical circuit, said representation including an approximation of the location of an edge of a conductor and the substrate along an edge portion of said conductor formed by said second part.

Optionally, the method comprises:

generating a first approximation of the location of said edge, analyzing the image for the presence of said first part and said second part, and in response to detecting the presence of said second part between said first part and said substrate revising said approximation of the location of the edge.

Optionally, where the image is monochrome, analyzing includes analyzing said monochrome image for differences in reflective intensities.

Optionally, where the image is polychromatic, analyzing includes analyzing said polychromatic image for differences in color.

Optionally, generating comprises generating an approximation of the location of an edge between a section of the first part and the substrate.

Optionally, revising comprises:

calculating a directed convex hull extending between various sections of the said approximation of an edge, and replacing the a section of the estimation of boundaries between the first part and the substrate with the directed convex hull.

Optionally, the directed convex hull extends between sections of the representation of boundaries that are at least partly adjacent a region identified as being a second part.

Optionally, the method includes identifying at least one point along the approximation of the location of boundaries between the first part and the substrate which is a corner. Optionally, the directed convex hull extends between a pair of corners.

Optionally, the directed convex hull extends between a corner and a point along the representation of boundaries which is located between said first part and said second part.

Optionally, the first part is metal that is not oxidized, and the second part is metal that is oxidized.

Optionally, the method includes inspecting the revised representation for defects according to a rule or a set of rules. Optionally, rule is a measure of distance between at least two approximate boundaries between conductor and substrate.

There is further provided, in accordance with an embodiment of the invention, a method for inspecting an electrical circuit comprising:

acquiring an image of the surface of the circuit;

approximating a location of an edge of a non-oxidized portion of a conductor in the circuit;

approximating a location of an edge between an oxidized portion of the conductor and a substrate in the circuit; and approximating a location of an edge of the conductor in response to the approximated locations of said edge of said non-oxidized portion and said edge of said oxidized portion; and measuring the width of the conductor with respect to said approximated edge thereof. Optionally, approximating the location of an edge between the oxidized portion and the substrate comprises generating a line segment extending between a pair of points along a contour defining said approximated location of an edge of said non-oxidized portion.

Optionally, the method includes detecting the location of at least two corners along the contour. Optionally, the method further includes:

extending a directed convex hull between the corners encompassing additional points located along the contour;

determining whether the material adjacent to the directed convex hull has an optical characteristic attributable to conductor; and if portions of the image adjacent to the directed convex hull have an optical characteristic attributable to conductor, revising the approximated location of an edge of said non-oxidized portions to include said directed convex hull, and if portions of the image adjacent to the directed convex hull have an optical characteristic not attributable to conductor, not replacing the approximated location of an edge of said non-oxidized portions with said directed convex hull.

In an embodiment of the invention, the optical characteristic attributable to conductor is an optical characteristic associated with oxidation of the conductor.

BRIEF DESCRIPTION OF FIGURES

Exemplary embodiments of the invention are described in the following description of non-limiting exemplary embodiments thereof, read in with reference to the figure attached hereto. Dimensions of components and features shown in the figures are chosen primarily for convenience and clarity of presentation and are not necessarily to scale.

FIG. 3 is a portion of a snapshot image corresponding to a pixel neighborhood surrounding a first candidate defect visible in FIG. 2;

FIG. 10A is the putative contour map shown in FIG. 9 and a convex hull calculated for an oxidation contour surrounding a candidate defect according to a first exemplary method of the invention;

FIG. 10B is the putative contour map shown in FIG. 9 and a convex hull calculated for an oxidation contour surrounding a candidate defect according to another exemplary method of the invention;

DETAILED DESCRIPTION OF EXEMPLARY EMBODIMENTS

Figure 1:
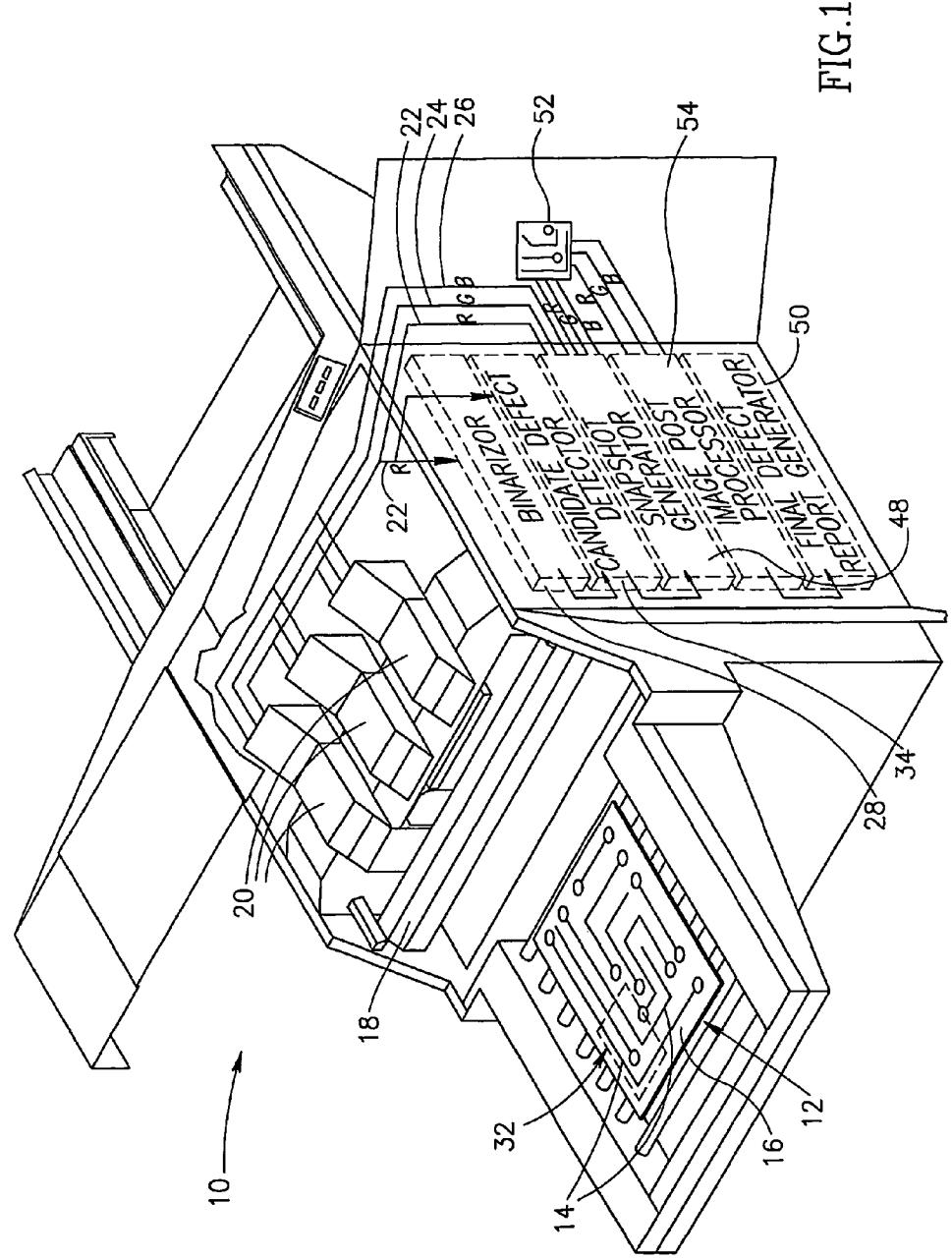
FIG. 1 is a simplified pictorial illustration of an automated optical inspection apparatus, useful for inspecting printed circuit boards, constructed and operative in accordance with an exemplary embodiment of the present invention.

Reference is made to FIG. 1 which is a simplified pictorial illustration of automated optical inspection apparatus constructed and operative in accordance with an exemplary embodiment of the present invention. Inspection apparatus 10 is operative to perform automated optical inspection of electrical circuits, such as are found on a PCB 12, having a multiplicity of metal conductors 14 disposed on a non-metal substrate 16. Although the present invention is generally described in the context of optical inspection of printed circuit boards, it is readily appreciated that the methods and apparatus described herein are generally applicable to the inspection of other patterned surfaces and in particular to the inspection of reticules and electrical circuits including, for example chip carriers, ball grid array substrates, tape bonding substrates, multi-chip modules, and hybrid circuit substrates. Reference herein to PCBs shall be deemed to additionally refer to other suitable forms of patterned surfaces and electrical circuits.

In a preferred embodiment of the invention, testing apparatus 10 includes an illuminator 18, preferably configured as described in PCT publication WO 99/66314, the disclosure of which is incorporated herein by reference, operative to illuminate PCB 12 during optical inspection. An array of cameras 20, preferably trilinear RGB 8000×3 element CCD sensors available from Eastman Kodak Corporation, is disposed to view a region on PCB 12 that is illuminated by illuminator 18. As PCB 12 is transported underneath illuminator 18, each of cameras 20 scan PCB 12 and preferably generate a 24-bit polychromatic image of PCB 12 formed from each of a separate but substantially mutually spatially coincidental red image output 22, green image output 24 and blue image output 26. Each of red image output 22, green image output 24 and blue image output 26 preferably corresponds to a gray level monochrome image of the inspected PCB in its respective spectrum.

Figure 2:
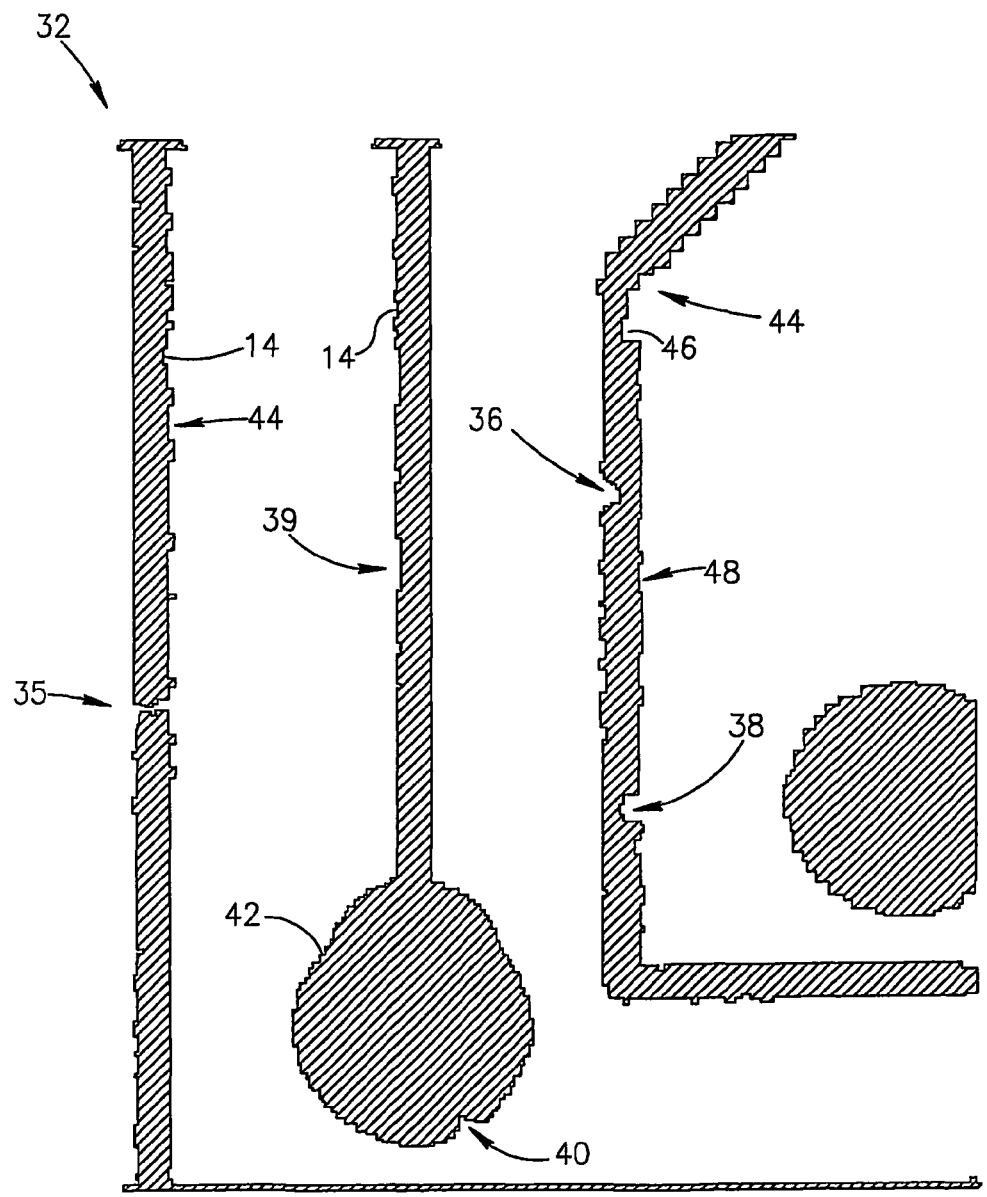
FIG. 2 is an enlarged binary representation of a portion of an electrical circuit on a printed circuit board corresponding to a printed circuit board shown in FIG. 1.

One of the gray level monochrome images, preferably from red output 22, is supplied to a binarizor unit 28 which preferably is operative to generate a binary image of electrical circuits on PCB 12 based on intensity values registered for pixels in the monochrome image. Preferably, in PCB inspection, red image output 22 is used because it exhibits an enhanced brightness gradient, relative to green image output 24 and blue image output 26, when inspecting copper deposited on typical PCB substrates. It is readily appreciated that red image output 22 includes less optical data about PCB 12 as compared with an image generated collectively from all three red, green and blue image outputs. In the binary image produced, regions determined to be substrate are assigned a value of 0 and images determined to be conductor are assigned a value of 1, or vice versa. Binarizor unit 28 is preferably operative to generate a binary image to sub-optical-pixel resolution, in accordance with methods shown and described in U.S. Pat. Nos. 5,774,572 and 5,774,573, the disclosures of which are incorporated herein by reference. An enlarged binary image of a portion of the electrical circuit of PCB 12, corresponding to region 32 in FIG. 1, is seen in FIG. 2.

The binary image of PCB 12 generated by binarizor 28 is provided to a candidate defect detector 34 which is operative to process the binary image and to identify therefrom various defects, such as various defects in the pattern formed by an electrical circuit on PCB 12. Candidate defect detector 34 preferably employs, at least in part, methods shown and described in PCT publication WO 00/19372, the disclosure of which is incorporated herein by reference, to analyze the binary image.

Candidate defect detector 34 also preferably includes a gray level processing pipeline (not shown) such as is described in U.S. Pat. Nos. 5,586,058 and 5,619,429, the disclosures of which are incorporated herein by reference. The gray level image employed preferably is derived from red image output 22. The gray level pipeline generally operates in parallel to binary image analysis performed in candidate defect detector 34. Preferably, candidate defect detector 34 classifies defects detected by binary and gray level analysis of PCB 12 into real defects and candidate defects.

Typical real defects which are detected by candidate defect detector 34 include the absence of features in an inspected PCB relative to a reference pattern, improper location of features in an inspected PCB relative to a reference pattern, extraneous features in an inspected PCB relative to a reference pattern. Additionally, some defects are typically classified by the candidate defect detector as real defects. Other defects which are typically classified as real defects, but which are not shown, include shorts in which two separate conductors are joined, pinholes in which a hole is found in the middle of a conductor, or scratches.

Typical defects which are classified by candidate defect detector 34 as candidate defects, and which are shown in FIG. 2, include a cut 35, a first line width violation 36, in which the width of a conductor 14 is determined to be insufficiently wide at a given point therealong, a second line width violation 38, and a candidate defect pad violation 40, in which a conductor pad 42 is determined to be too small or improperly shaped.

Other deformities that may be seen in FIG. 2, but which do not necessitate classification as a real or candidate defect, include minor line width violations 48, in which the width of a conductor 14 is determined to be less than a nominal specified line width, but not to the extent necessary to constitute a candidate defect line width violation such as first line width violation 36 or second line width violation 38.

Based at least in part on analysis of a reduced data image, such as a binary image produced by binarizor 28, candidate defect detector 34 generates an initial defect report specifying the type and location of real defects and candidate defects suspected of being defective, on PCB 12. The initial defect report from candidate defect detector 34 is provided to a snapshot generator 48 and to a final defect report generator 50.

Snapshot generator 48, in addition to receiving the initial defect report from candidate defect detector 34, also receives a full optical data image of PCB 12. Preferably, the full optical data image comprises each of the red image output 22, green image output 24 and blue image output 26 received from cameras 20 respectively.

For defects which are deemed candidate defects, for example line width violations 36 or 38, or pad violation 40 seen in FIG. 2, snapshot generator 48 generates and outputs a snapshot 52 of a neighborhood surrounding each such candidate defect. Snapshot 52 preferably comprises reflected light intensity values registered on pixels in cameras 20 for red, green and blue spectra, as received from each of the red image output 22, green image output 24 and image output 26 respectively. In exemplary embodiments, snapshot 52 includes an array of pixel values for between 50×50 and 150×150 pixels, and typically between about 90×90 and 100×100 pixels. The size of snapshot 52 may be fixed or determined dynamically in response to the size or type of a candidate defect, it being preferable to generate a snapshot 52 that is as small as possible while still including necessary processing information.

Figure 3:
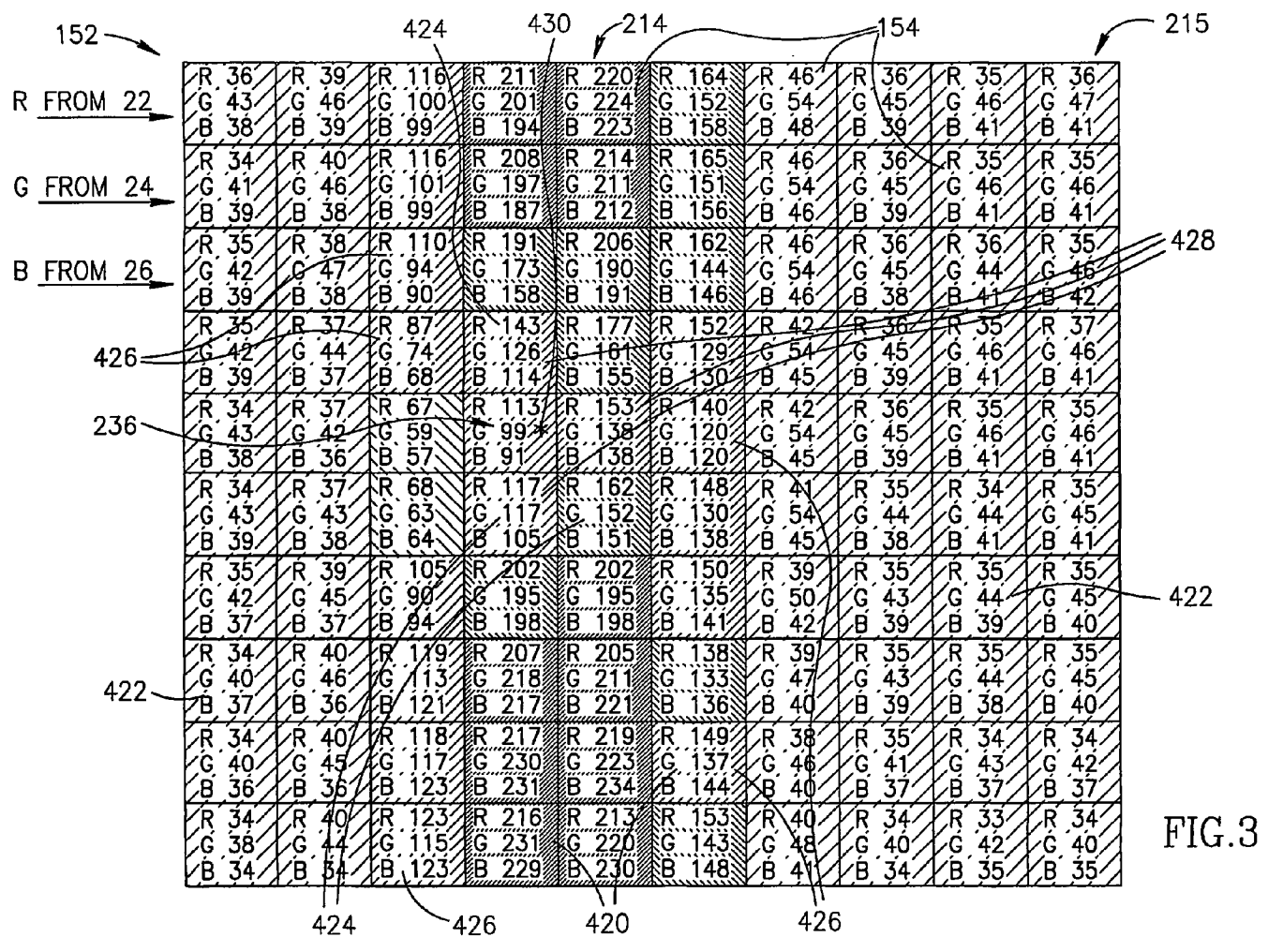

Reference is now made to FIG. 3 in which there is shown a portion 152 of snapshot 52. Snapshot portion 152 corresponds to a pixel neighborhood immediately surrounding candidate major line width violation 36 shown in FIG. 2. As seen, each pixel 154 in snapshot portion 152 includes three numerical values, an "R" value representative of reflective intensity for red, a "G" value representative of reflective intensity for green, and a "B" value representative of reflective intensity for blue. The "R", "G" and "B" values seen for each pixel 154 range between 30 and 225 and correspond to the light intensity values registered by pixels in cameras 20 at a given sampling point on PCB 12 which output to each one of red image output 22, green image output 24 and blue image output 26 respectively. For the purpose of illustration of the principals of the invention, the pixel values are shown superimposed over a gray level representation of a portion PCB 12 in which there is seen a conductor portion 214, adjacent substrate portion 215 and a candidate defect 236, corresponding to candidate line width violation 36 shown in FIG. 2.

Referring back to FIG. 1, snapshot 52 is supplied to an image post processor 54, a preferably software based image processing package, which is operative to receive and to analyze the snapshot 52 and output to final defect report generator 50 a report of the type and location of real defects that are found from analysis of snapshot 52. The details of a preferred method for processing snapshot image 46 are discussed in greater detail hereinbelow with respect to FIGS. 4–6.

Final defect report generator 50 receives defect reports from candidate defect detector 34 and from post-processor 54, and combines the report to produce a combined report of each real defect that is detected on PCB 12. It is appreciated that report generator 50 may be configured alternatively to issue additional reports of specious candidate defect, for example oxidation.

From the above description of the system of the present invention, it is appreciated that binarizor 28 and candidate defect detector 34 generally form a fast, preferably hardware, pipeline that preferably prepares and analyzes reduced data optical images to quickly identify regions on PCB 12 which include real defects and regions which include candidate defects in the electrical circuit pattern situated on PCB 12. Snapshot generator 48 thus receives a report of candidate defect regions, and typically proceeds to prepare a robust full data image, preferably a full color image, of a neighborhood surrounding each candidate defect, for example for use in additional image processing operations or for viewing by an operator. In exemplary embodiments, each snapshot 52 is derived from the same raw image inputs from which reduced data images analyzed by candidate detector 48 are derived.

Typically, post processor 54 is implemented in software, which although typically slower than dedicated hardware, has a higher degree of flexibility in applying different inspection algorithms. For example, a software processor may be operative to dynamically define regions on PCB 12 suspected of including a candidate defect. The software may be further operative to apply one or more inspection algorithms to the dynamically defined region, as triggered by the type of candidate defect, which algorithms are chosen from among a number of available algorithms as being the best algorithm available to determine whether a particular candidate defect is specious or real.

Additionally, a software based processor typically is able to achieve a significantly higher accuracy in identifying real defects, as compared with the fast hardware processing employed by candidate defect detector 34, by analyzing a data robust image. Thus in order to maximize the superior image processing power of post processor 54 in view of its relative slowness compared to a candidate defect detector 34, software based image post processing is typically restricted only to those areas which are identified as being regions surrounding candidate defects. Such regions may be dynamically defined in response to discovery of candidate defects by candidate defect detector 34. Furthermore, in order to efficiently utilize post processing resources, post processor 54 may be configured so as not to inspect regions surrounding defects that are classified by candidate defect detector 34 as being a real defect.

Figure 4:
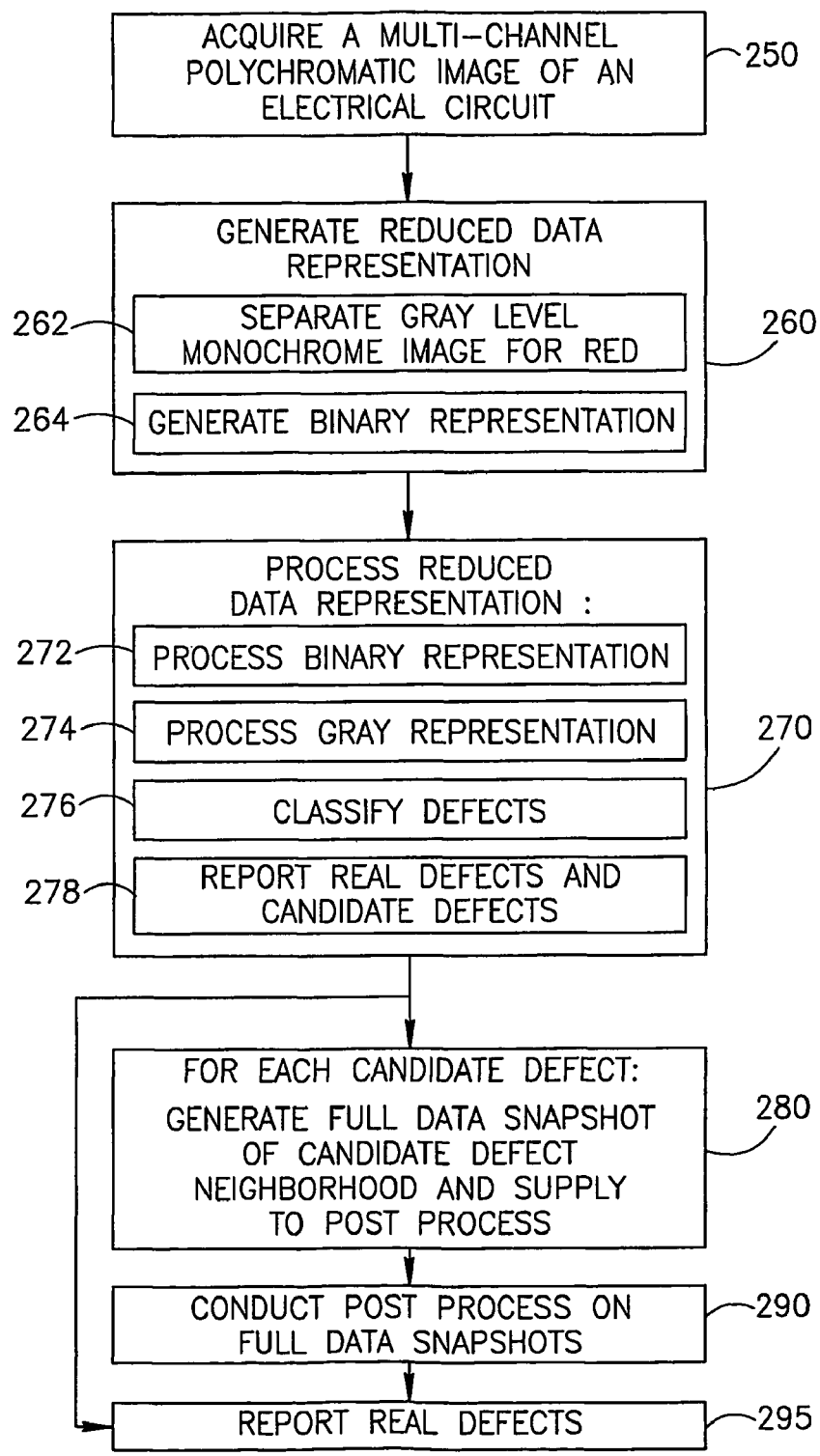
FIG. 4 is a flow diagram schematically illustrating principal acts in a preferred method, operative in the environment of the apparatus shown in FIG. 1, for identifying and processing defects in PCBs.

Reference is now made to FIG. 4 which is a flow diagram schematically illustrating principal acts in an exemplary method, operative in the environment of the apparatus shown in FIG. 1, for identifying and processing defects in PCBs. The preferred method includes the following:

Block 250: A multi-channel input image of a PCB 12, or other patterned object suitable to be inspected, is acquired preferably using apparatus described with reference to FIG. 1. The image acquired is preferably a 24-bit or 48-bit color polychromatic image of PCB 12 and is formed from separate but generally spatially coincidental red image output 22, green image output 24 and blue image output 26. Each of the respective red, green and blue images preferably are monochrome gray level images in a respective spectral range and together they form a full color image of optical data derived from PCB 12.

Block 260: A reduced optical data image or representation of PCB 12, enabling quick image processing, is generated. At 262 a monochrome red gray level image portion of the polychromatic image acquired at 250 is separated from the polychromatic image. At 264, the red image portion is processed, for example, in binarizor 28 of FIG. 1, to generate a representation of the electrical circuit on PCB 12. The binary representation is generated by binarizor 28 preferably using methods shown and described in the above referenced U.S. Pat. Nos. 5,774,572 and 5,774,573, to produce a binary representation that has a higher resolution than the optical resolution of cameras 20 (FIG. 1).

Block 270: The reduced data representation generated at 260 is supplied for example, to candidate defect detector 34 of FIG. 1, where it is analyzed and processed to identify and classify real defects, candidate defects and specious defects in PCB 12. The image is ideally processed "on the fly" in a real time processing system as is known in the art, for example using an InSpire™ 9060 automated optical inspection system, available from Orbotech of Yavne, Israel. Block 270 typically includes a binary image process 272, and a gray level image process 274. The binary image process typically applies a combination of rules specifying the desired shape, position and location of features in the pattern on PCB 12, and image analysis, for example erosion/dilation operations, to morphologically analyze the pattern. The erosion/dilation operations preferably employ methods which are described in greater detail in the above referenced WO 001/9372.

It is appreciated that the binary image process 272 and gray level image process 274 typically are parameterized to detect a greater number of defects than actually exist on PCB 12. Thus block 270 generally includes defect classification 276 in which defects are classified into real defects which indicate candidate defects which are defects for which additional processing operative to differentiate between real defects or specious defects is available, and other defects which to a very high degree of probability are real defects or for which no additional processing is available. Some deformities and anomalies may be filtered out entirely as being specious defects. At 278 a defect report is generated. The defect report preferably provides an initial indication of the type of each defect, for example line width violation, cut, short, extraneous feature, missing feature, and its respective location. The report is typically provided to snapshot generator 48 and to final defect report generator 50 (FIG. 1).

Block 280: Snapshot generator preferably generates a snapshot of a pixel neighborhood surrounding each candidate defect reported at 270. It may also be useful in some operations to generate snapshots for various non-candidate defects, for example for the purpose of calibrating candidate defect detector 34 or for trouble shooting.

In some embodiments of the invention, the snapshot 52 is generated from the same raw data image from which the reduced date images are generated at 260. Snapshot image 52 generated at 280 typically includes the optical data collectively contained in red image output 22, green image output 24 and blue image output 26, spatially restricted to a neighborhood surrounding a candidate defect. Alternatively, a binary image may be generated from a first image input, while snapshot image is generated from a second image input (not shown) separate from the first image input and including a larger amount of optical information, for example a very high resolution 24 bit, full color image.

Block 290: Snapshots are processed and analyzed, for example, in image post processor 54. The snapshot images contain at least some optical data about the optical characteristics of the electrical circuit which is additional to the data included in the reduced data images generated at 260. A report of real defects detected in the image post process at 290 is output to final defect report generator 50 (FIG. 1).

Block 295: A complete report of defects present in the electrical circuit is generated from the report output at 278 and from the output of block 290.

Figure 5A:
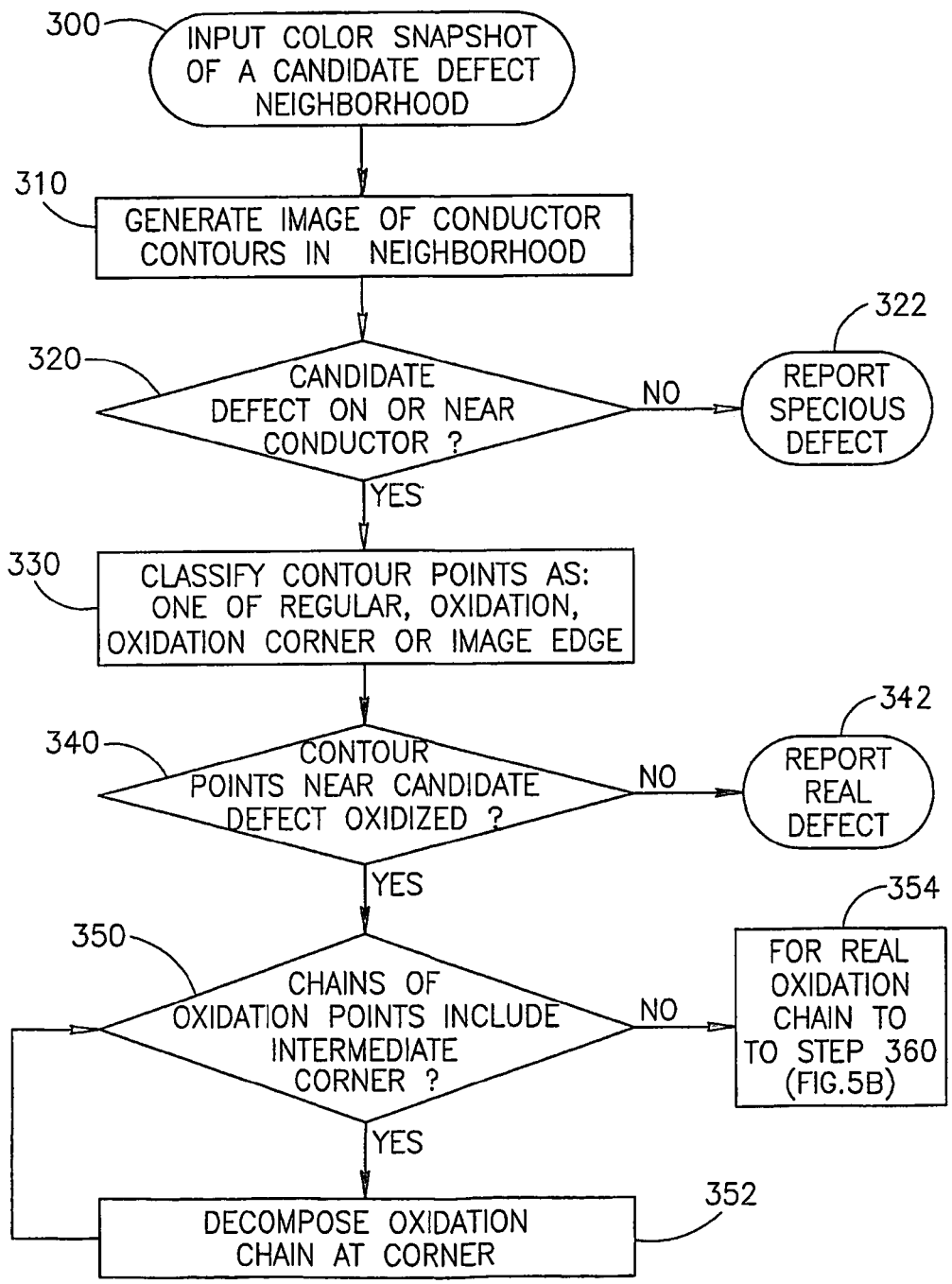
FIG. 5A and FIG. 5B are a flow diagram illustrating the principal acts in a preferred post process operation useful in the inspection of electrical circuits on printed circuit boards.
Figure 5B:
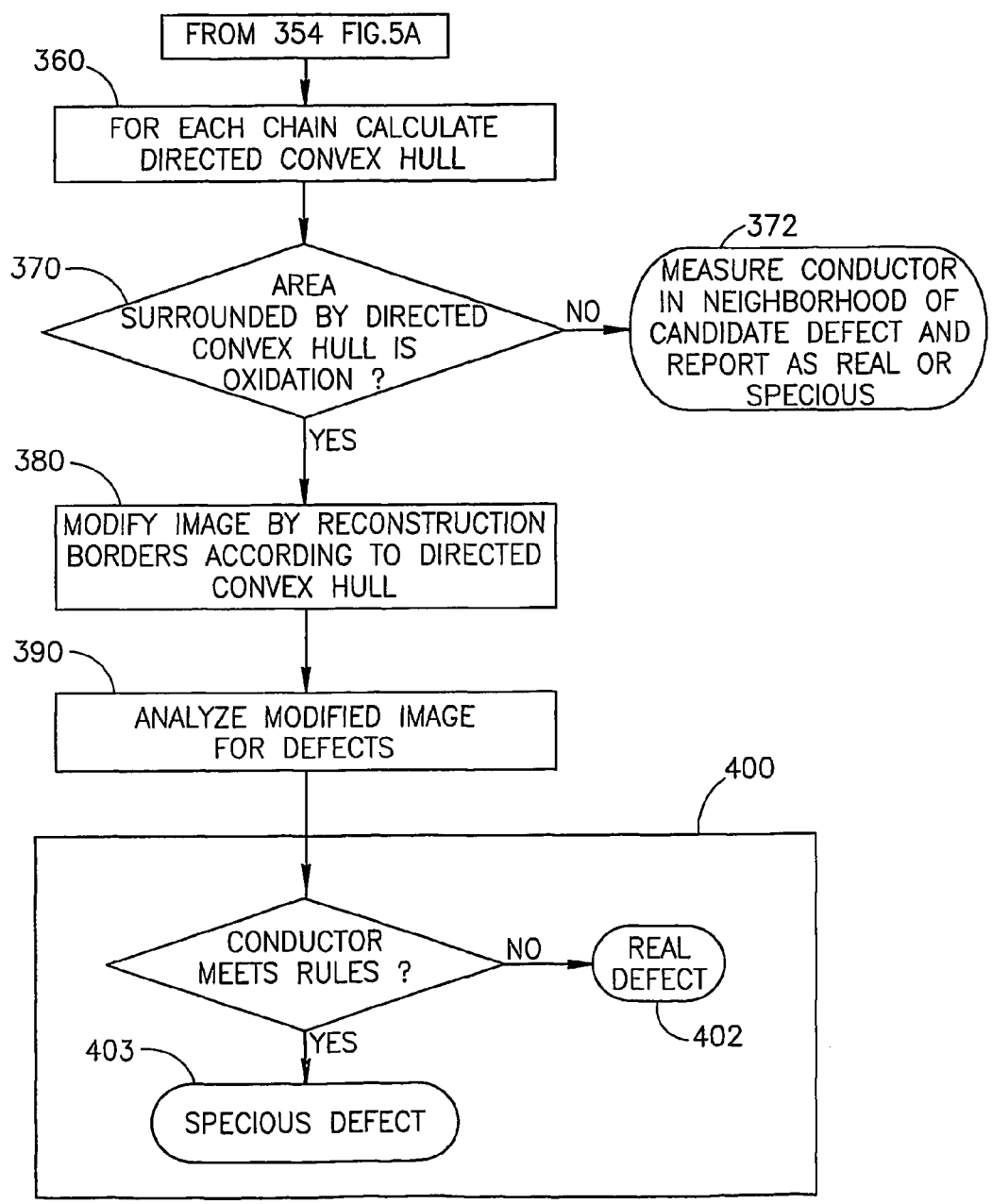

Reference is now made to FIG. 5A and FIG. 5B which are a flow diagram showing the principal acts in a preferred post process operation for the inspection of electrical circuits on printed circuit boards, preferably employed in block 290. The post process operation shown in FIGS. 5A and 5B is particularly suited to evaluating candidate defects that are suspected line width violations on conductors 14.

In conventional inspection methods, line width violations, and other similar defects such as pad violations, typically are caused by insufficient copper, or by a misinterpretation of oxidized copper as being missing copper. The preferred post process methods, shown and described with reference to FIGS. 5A and 5B, employs various image analysis methods to evaluate whether a candidate line width violation at a given location is the result of insufficient copper, or merely a misinterpretation of oxidation as substrate that causes a false alarm.

It is readily appreciated that the post process methods described hereinbelow are exemplary of post processing methods that may be employed to analyze images of PCBs having a greater quantity of data than the data present in reduced data representations, such as are generated in block 260 and analyzed in block 270 (FIG. 4). It is also readily appreciated that a post process coming within the scope of the invention may employ various methods that are operative to analyze images which have an increased quantity of optical data relative to the images used to identify candidate defects, for example as contained in color images, and that block 290 may additionally employ a dynamic algorithm adapter which classifies the type of candidate defect and then applies an appropriate algorithm to a particular type of candidate defect. For example, a first algorithm may be applied to a line width defect, while a second different algorithm may be applied to a candidate pad defect, or to a suspected copper splash such as a possibly extraneous isolated island of copper.

An exemplary post processing method which is operative to evaluate the existence of oxidation and to determine the presence of real defects on conductors 16 (FIG. 1) that are oxidized, preferably includes the following:

Block 300: A full color snapshot image of a pixel neighborhood surrounding a candidate defect, such as snapshot 52 in FIG. 1, is processed, for example, in a post processor such as post processor 54. As noted from the preceding discussion, the snapshot preferably is prepared from raw data that includes values for optical pixels in each of the red image outputs 22, green image outputs 24 and blue image outputs 26. Thus, snapshot 52 typically includes optical data that is not included in the reduced data representation employed by candidate defect detector 34 to detect candidate defects. Each snapshot image 52 is restricted to a pixel neighborhood surrounding a candidate defect. Preferably, the neighborhood is large enough to include the full extent of the candidate defect.

Block 310: Initially, a representation of contours, ideally for all of snapshot image 52, is generated. Contours represent putative boundaries between conductor and substrate, and in electrical circuits comprising copper conductors, contours are typically generated from analysis of data in red image input 22 only. An exemplary method for generating contours, in which the locations of contours are approximated based on information contained in red image output 22, is described hereinbelow in greater detail with reference to FIGS. 6–9.

Block 320: A candidate defect, for example candidate defect 236 (FIG. 3), is evaluated, preferably with reference to the location of contours as calculated in block 310. A precise location of a candidate defect is provided, for example, by candidate defect detector 34, and typically is represented by a point. A snapshot image may include a plurality of conductors. The method preferably evaluates whether a candidate defect is on a conductor or near a conductor. If a candidate defect is located outside and not near a conductor to within a predetermined threshold or certainty, then the defect is deemed an image anomaly; a specious defect report 322 is made, and the post process exits with respect to the particular candidate defect. If a candidate defect is inside a conductor, or outside a contour but near a conductor to within a predetermined distance, then processing is restricted only to a pixel neighborhood immediately surrounding the conductor in which the candidate defect is located; and the post process proceeds to block 330.

Block 330: In accordance with a preferred embodiment of the present invention, contour points in the contour representation generated at 310, may be classified, as one of (i) a regular contour point, (ii) an image boundary contour point, (iii) an oxidation contour point, (iv) a corner contour point, or (v) an oxidation corner. Classification is based preferably on analysis of the data obtained from the collection including red image output 22, green image output 24, and blue image output 26, although any of outputs 22, 24 and 26 may be used alone or in a sub-combination. It is readily appreciated that the combination of red output 22, green image output 24 and blue image output 26 contribute optical information about PCB 12 that is not present any single output.

Block 340: Contour points in the pixel neighborhood are evaluated for the existence of oxidation in the neighborhood of the candidate defect, in accordance with a preferred embodiment of the present invention, if contour points in the vicinity of the candidate defect are not oxidized, then the candidate defect is deemed a real defect. Alternatively, a region neighboring a candidate defect is analyzed to determine the presence of oxidation, and if oxidation is not found then the candidate defect is deemed to be a real defect.

For each real defect, a real defect report 342 is issued, and the post process exits for each such candidate defect. Alternatively, a defect may be passed on for further processing, for example with another algorithm, to evaluate whether it is a real or specious defect. If contour points in the vicinity of the candidate defect are oxidized, or if oxidation is found in a region neighboring a candidate defect, then the present post process continues.

Block 350: Chains of oxidation contour points in the pixel neighborhood are evaluated for the existence of a corner in the chain. A chain of oxidation contour points is any collection of contiguous oxidation contour points along a contour that includes at least three oxidation points. A preferred method for ascertaining the presence of a corner along a contour is described in copending PCT patent application PCT/IL00/00434 entitled, Optical Inspection System, the disclosure of which is incorporated herein by reference. Typically, oxidation chains that lie on either side of a corner are separately processed. Thus if a corner contour point is located along a chain of oxidation contour points, the oxidation chain is decomposed at the corner contour point at block 352. For each collection of oxidation contour points on either side of the corner, the process proceeds to block 354 and proceeds to separately analyze each chain of oxidation contour points.

Block 360 (FIG. 5B): A directed convex hull is calculated for each chain of oxidation points in snapshot 52. A convex hull of a collection of points is a polyline connecting the smallest convex set of points in the collection which defines a region containing all of the points. The directed convex hull is a section on the convex hull which connects two extreme contour points for which all contour points are either located along the directed convex hull or on the conductor side thereof. Methods for computing a convex hull and a directed convex hull are very well known to persons skilled in the art of computational geometry. A suitable method is described at M. deBerg, M. van Kreveld, M. Uvermars and V. Schwarzkopf, *Computational Geometry*, Springer 1997. Preferably, the extreme points are corner points, or oxidation points that neighbor a regular contour point.

Block 370: The area adjacent to a directed convex hull along the conductor side of the contour is verified as being oxidized copper, or otherwise suitable to be considered copper (collectively termed herein oxidized copper), preferably by color analysis of selected pixels surrounding the contour.

Alternatively, a region adjacent to a directed convex hull may be evaluated to determine whether it is to be considered laminate or copper relying solely on inputs from one of the red image output 22, green image output 24 or blue image output 26.

Figure 14:
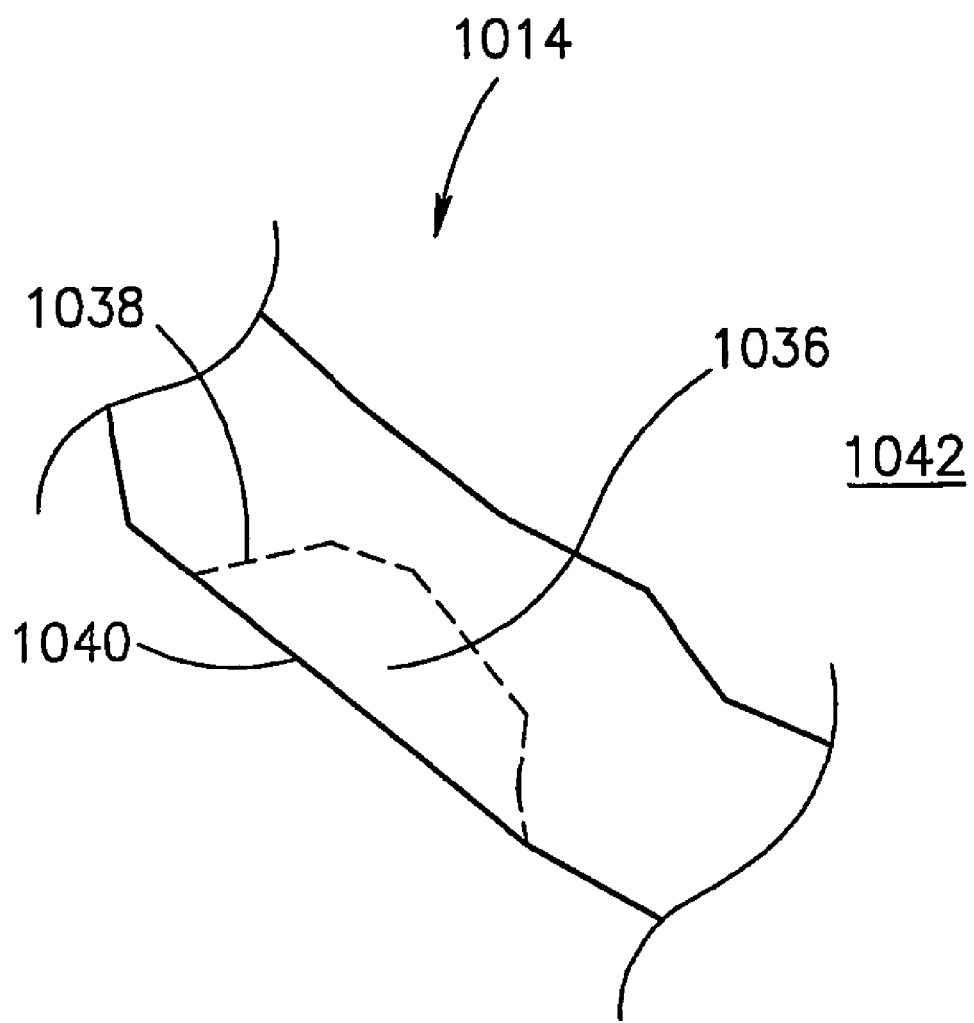
FIG. 14 shows a portion of a conductor in an electrical circuit having a candidate defect in an area defined by a convex hull.

Reference is made to FIG. 14 in which there is seen a portion of a conductor 1014 having a candidate defect 1036 in an area defined by a convex hull 1038 and having a directed convex hull portion 1040. Conductor 1014 is disposed on a background of substrate 1042.

A decision tree in accordance with a preferred embodiment of the invention for determining whether a region inside convex hull 1038 is laminate or oxidized copper, is as follows:

Definitions:

COP=the average intensity of pixels imaging portions of conductor 1014 which are copper.

LAM=the average intensity of pixels imaging portions of conductor 1014 which are laminate.

The intensities of pixels imaging an electrical circuit under test are normalized so that COP=1 and LAM=0. Thus, for example, an intensity that is midway between COP and LAM will be assigned a value of 0.5.

In addition the following values A–E, are defined:

A=the maximum intensity gradient along directed convex hull 1040, and in a direction normal thereto.

B=the minimum intensity gradient along directed convex hull 1040, and in a direction normal thereto.

C=the average intensity of pixels in red image output 22 (FIG. 1) inside convex hull 1038.

Ratio R=B/A.

S=Ratio+C

Area=region inside convex hull 1038

In an exemplary situation, the classification procedure is performed at one of two user definable sensitivities, a low sensitivity or a high sensitivity, for detection of copper. The sensitivities refer to the sensitivity at which an inspection system, for example the Inspire™ 9060 available from Orbotech Ltd. of Israel, identifies a pixel as being correlated to copper or to substrate. At a low sensitivity setting, the inspection system is less likely to identify a pixel as being correlated to copper than at a high sensitivity setting. Thus, when set at high sensitivity, some pixels that may be considered as correlating to copper, for example pixels imaging oxidized copper, would not be considered as correlating to copper if the system had been operated at its low sensitivity. The choice of whether to use the low sensitivity or high sensitivity is made empirically based on the level of sensitivity chosen by a user and desired response to oxidized regions of copper.

If C<0.05 then Area=laminate; else
if C>0.25 then Area=copper; else
Determine whether Area is copper or laminate in accordance with either of following low sensitivity or high sensitivity decision trees:

For LOW sensitivity:
if S<1.2=>Area=copper else
if B<25=>Area=laminate else
if B>55=>Area=copper else
if R>1.2=>Area=copper else
Area=laminate.

For HIGH sensitivity:
if S<1=>Area=copper else
if B<20=>Area=laminate else
if B>50=>Area=copper else
if R>1=>Area=copper else
Area=laminate.

The procedure may vary somewhat with other equipment. However, the example will give clear guidance to a person of skill in the art as to how the invention can be applied using different equipment.

If the region tested, for example the region inside convex hull 1038, is not oxidized copper, then the width of the conductor is measured and a report 372 of real or specious defect is made as appropriate, otherwise the post process continues.

Block 380 (FIG. 5B): If it is verified in block 370 that the region adjacent to the directed convex hull includes oxidized copper, then the representation of contours generated in block 310 is modified by replacing the existing contour with a contour that includes the directed convex hull extending between extreme points.

Block 390: The modified image obtained in block 380 is analyzed for defects. Preferably, the region surrounding a modified contour is tested again to verify the existence of oxidized copper. Upon verification, the distance between two opposite sides of the contours, which represents an estimation of the location of opposite edges of the copper conductor, is computed and then utilized to determine the presence of a real defect or specious defect due to oxidation.

Block 400: A decision tree is followed to handle real and specious defects analyzed at 390. If a conductor portion, modified as described above, fails to meet a set of rules governing its structure, then a real defect report 402 is issued. At this point, the real defect may be passed on for further processing, for example by another algorithm, or the post process exited and the defect appropriately marked. If the modified conductor portion meets the rules, then the defect is deemed a specious defect 403 and subsequently ignored. Alternatively a specious defect is reported.

It is appreciated that if a conductor portion includes multiple oxidation chains, analysis of the image performed at block 390 is done after contours are reconstructed for each of the oxidation chains in the image.

Reference is now made to FIGS. 3 and 6–12 to further illustrate the post process hereinabove described.

Referring now to FIG. 3, a snapshot portion 152 surrounding a candidate defect 236 is shown. For the purpose of simplifying the illustration, it is noted that FIG. 3 is restricted to show only a portion of the full snapshot 52. Candidate defect 236 is a candidate line width violation detected by candidate defect detector 34.

In the vicinity of candidate defect 236, conductor 214 is oxidized. In FIG. 3, pixels in regions of non-oxidized copper, for example pixels 420, register relatively high values of reflectivity in the order of 210 to 220 in the "R" channel received from red image output 22 and are darkly shaded. Pixels in regions of substrate, for example pixels 422, register relatively low values of reflectivity, in the order of 35 for the "R" channel and are lightly shaded. Pixels in regions of oxidized copper, for example pixels 424, and pixels along borders between copper and substrate, for example pixels 426, all register intermediate values of reflectivity in the order of 65–195 in the "R" channel, and are intermediately shaded. Pixels for regions of oxidized copper, for example pixels 428, exhibit subtle differences in the "G" channel from green image output 24 and in the "B" channel from blue image output 26 compared to non-oxidized conductor. Possibly analysis of subtle differences of pixel values in the "G" and "B" channels, in addition to consideration of pixel values in the "R" channel, may be helpful in distinguishing between regions of oxidized copper from edge regions.

It is appreciated that the intensities shown in FIG. 3 are chosen for convenience of illustration and that intensities for pixels imaging copper, pixels imaging substrate, pixels imaging borders between copper and substrate, and pixels imaging oxidized copper can be different from those shown.

Snapshot images are typically provided with a candidate defect location indication 430 which indicate the particular location of a candidate defect determined at Block 270 of FIG. 4. Preferably, the entire snapshot 52 is analyzed for defects, however in applications in which processing time is limited, it is readily appreciated that analysis of the snapshot image may be restricted to a portion of the snapshot in a neighborhood having a radius of N pixels surrounding candidate defect location indication 430, where the value N typically is set, either statically or dynamically, as a system parameter. When analysis of the image is limited to a neighborhood immediately surrounding candidate defect location indication 430, the size of the neighborhood is chosen to be sufficiently large to encompass all of a candidate defect 236 and closely adjacent regions of conductor 214 and substrate 215.

Figure 6:
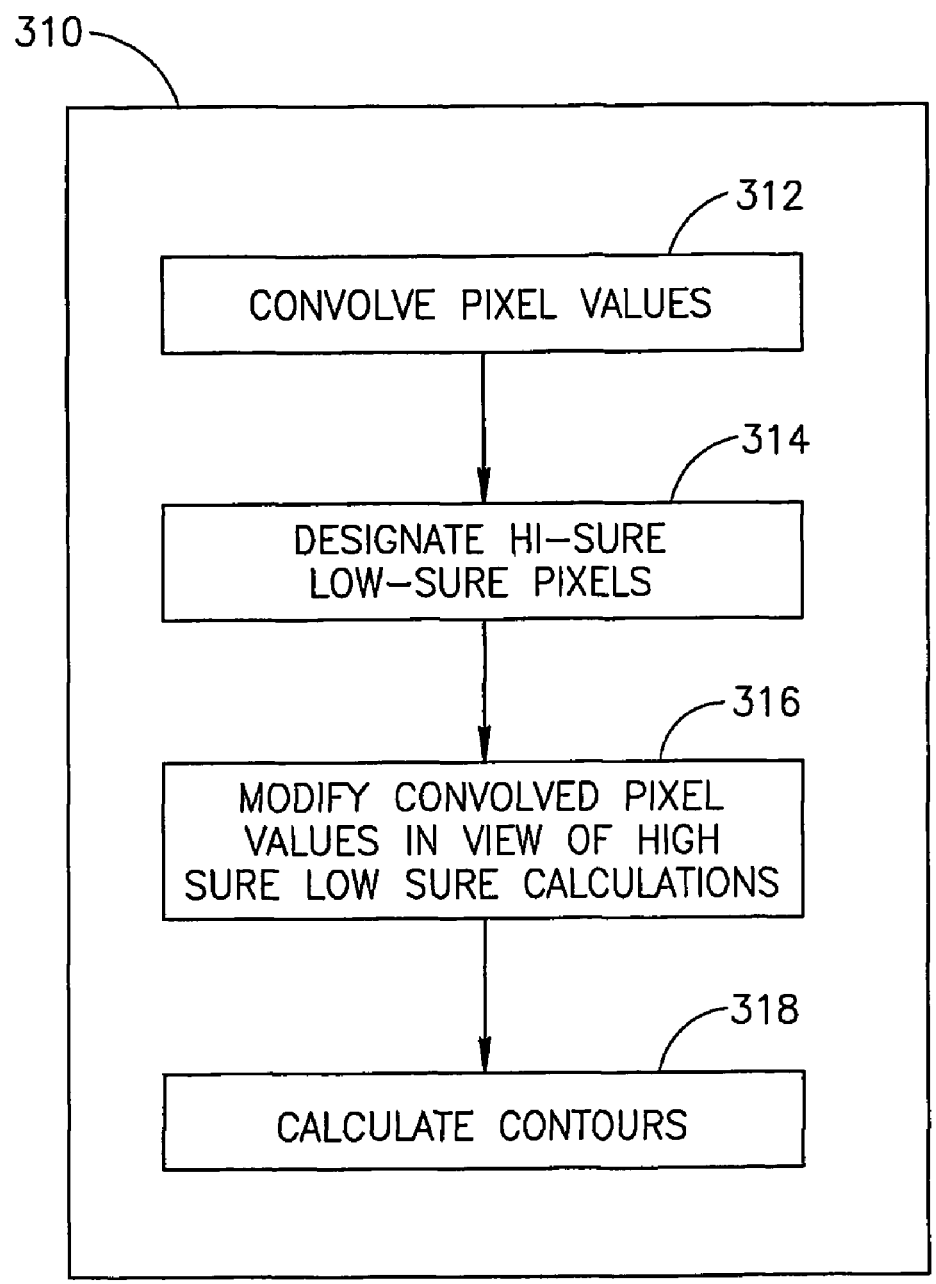
FIG. 6 is a flow diagram schematically illustrating principal acts in an exemplary method for computing contours in an image to within sub-pixel accuracy.

Reference is made to FIG. 6 which is a flow diagram schematically illustrating principal acts of an exemplary method, employed, for example in block 310 (FIG. 5A), to compute contours in an image portion to within sub-pixel accuracy. Operation of the preferred method of FIG. 6 is referenced to FIG. 3.

Block 312: The "R" intensities of all pixels 154 in snapshot portion 152 preferably are convolved with at least one edge-determining kernel. The convolution generates a value, hereinafter referred to as a "convolution value", for each pixel 154 that is subsequently employed to identify a point along a putative boundary between conductor 214 and substrate 215 in image portion 152.

Typically, the kernel generates a convolution value for each pixel 154 that is the convolution of the R intensity values at the location of the pixel with two-dimensional approximation of the second derivative of a Gaussian function, for example using a difference of Gaussians methodology substantially as described in U.S. Pat. No. 5,774,572 for an Automatic Visual Inspection System, the disclosure of which is incorporated by reference. The convolution may be performed by application of a kernel or by sequential orthogonal convolution. The difference of Gaussians approximation may be performed for any suitable combinations of pixel neighborhoods, for example 5×5–1×1 neighborhoods, or 9×9–3×3 neighborhoods. Other edge detection methodologies, as generally described in D. Marr, *Vision*, Freeman & Co., New York, 1982, may also be employed.

A kernel for effecting a two-dimensional approximation of the second derivative of a Gaussian function has the form:

$$\begin{matrix} 0.0039 & 0.0156 & 0.0234 & 0.0156 & 0.0039 \\ 0.0156 & 0.0625 & 0.0938 & 0.0625 & 0.0156 \\ 0.0234 & 0.0938 & -0.8594 & 0.0938 & 0.0234 \\ 0.0156 & 0.0625 & 0.0938 & 0.0625 & 0.0156 \\ 0.0039 & 0.0156 & 0.0234 & 0.0156 & 0.0039 \end{matrix}$$

in which a convolution value for a pixel corresponding to the central cell of the kernel is the sum of reflective intensity values for neighboring pixels, corresponding to cells in the kernel, wherein each intensity value is multiplied by a convolution value taken from a corresponding cell in the kernel.

In a preferred implementation, the kernel is separable. The above kernel can then be written as the product of the following kernels:

$$\begin{matrix} 0 & 0 & 0.0625 & 0 & 0 \\ 0 & 0 & 0.25 & 0 & 0 \\ 0 & 0 & 0.375 & 0 & 0 \\ 0 & 0 & 0.25 & 0 & 0 \\ 0 & 0 & 0.0625 & 0 & 0 \end{matrix}$$

and $$\begin{matrix} 0 & 0 & 0 & 0 & 0 \\ 0 & 0 & 0 & 0 & 0 \\ 0.0625 & 0.25 & 0.375 & 0.25 & 0.0625 \\ 0 & 0 & 0 & 0 & 0 \\ 0 & 0 & 0 & 0 & 0 \end{matrix}$$

Which thereafter is summed with the following kernel:

$$\begin{matrix} 0 & 0 & 0 & 0 & 0 \\ 0 & 0 & 0 & 0 & 0 \\ 0 & 0 & -1 & 0 & 0 \\ 0 & 0 & 0 & 0 & 0 \\ 0 & 0 & 0 & 0 & 0 \end{matrix}$$

Figure 7:
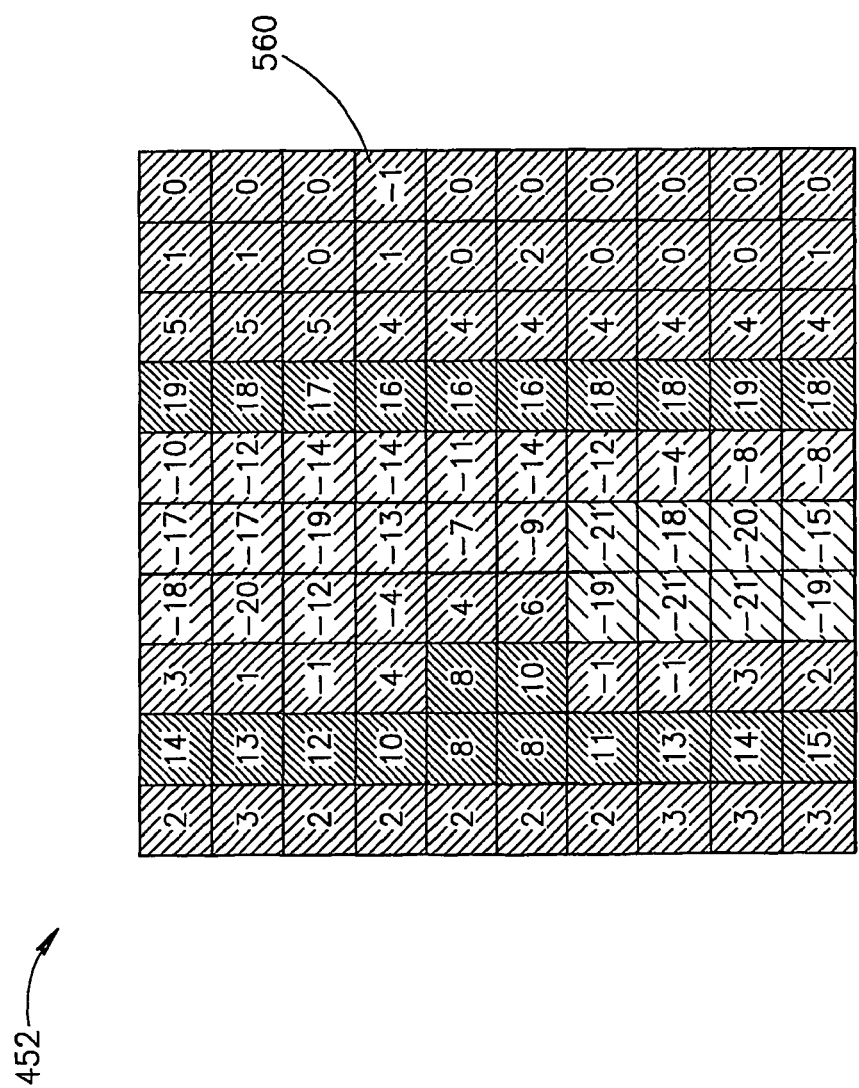
FIG. 7 is a convolved pixel value map of the image of FIG. 3, showing convolved pixels values calculated by application of an edge-determining kernel.

Reference is made to FIG. 7 which shows a convolved pixel value map 452 for image portion 152, calculated by application of the preceding edge-determining kernel.

Block 314: Pixels in snapshot portion 152 are generally designated as being high-sure, low-sure or transitional. A high-sure pixel is a pixel which is positively determined to be copper by analysis of the reflectivity coefficients of pixels in snapshot portion 152. A low-sure pixel is a pixel which is positively determined to be substrate by analysis of the reflectivity values of pixels in snapshot portion 152. A transitional pixel is a pixel which determined to be neither high-sure nor low-sure from analysis of the reflectivity values of pixels in snapshot portion 152.

In accordance with an exemplary method, user defined pixel value thresholds are employed to evaluate whether a pixel is high-sure, low-sure or transitional. Thus, if a pixel and all of its eight adjoining neighbors are above a high-sure threshold value, then the pixel is deemed a high-sure pixel. If a pixel and all of its eight adjoining neighbors are below a low-sure threshold value, then the pixel is deemed a low-sure pixel. If the values of a pixel or any of its neighbors are above and below the high-sure value, or if the values of a pixel or any of its neighbors are above and below the low-sure value then the pixel is a transitional pixel. The high-sure threshold value and the low-sure threshold value may be different values, or only a single value may be employed.

In the example shown in FIGS. 3–8 with respect to image portion 152, a single threshold value is applied to distinguish between high-sure and low-sure regions, and for the purposes of illustration it is set at 80. Thus a pixel is a high-sure pixel only if its value, and the values of all of its eight neighbors, exceed 80, while a pixel is low-sure if its value, and the values of all of its eight neighbors, are less than 80. All other pixels are transitional pixels.

It is appreciated that the blocks 312 and 314 may be performed in the order shown, or in reverse order, or in parallel.

Block 316: The pixels values in convolved pixel value map 452 (FIG. 7) are checked and revised in view of high-sure and low-sure calculations. Additionally, in order to ensure that contours are formed as a closed loop, the two most extreme pixels in each row and column preferably are designated low-sure, regardless of their actual value. It is readily appreciated that the attribution of a low sure designation may be performed by conversion of values in extreme rows in an actual image being analyzed, or by adding to the image additional rows and columns having an appropriate low-sure value.

Figure 8:
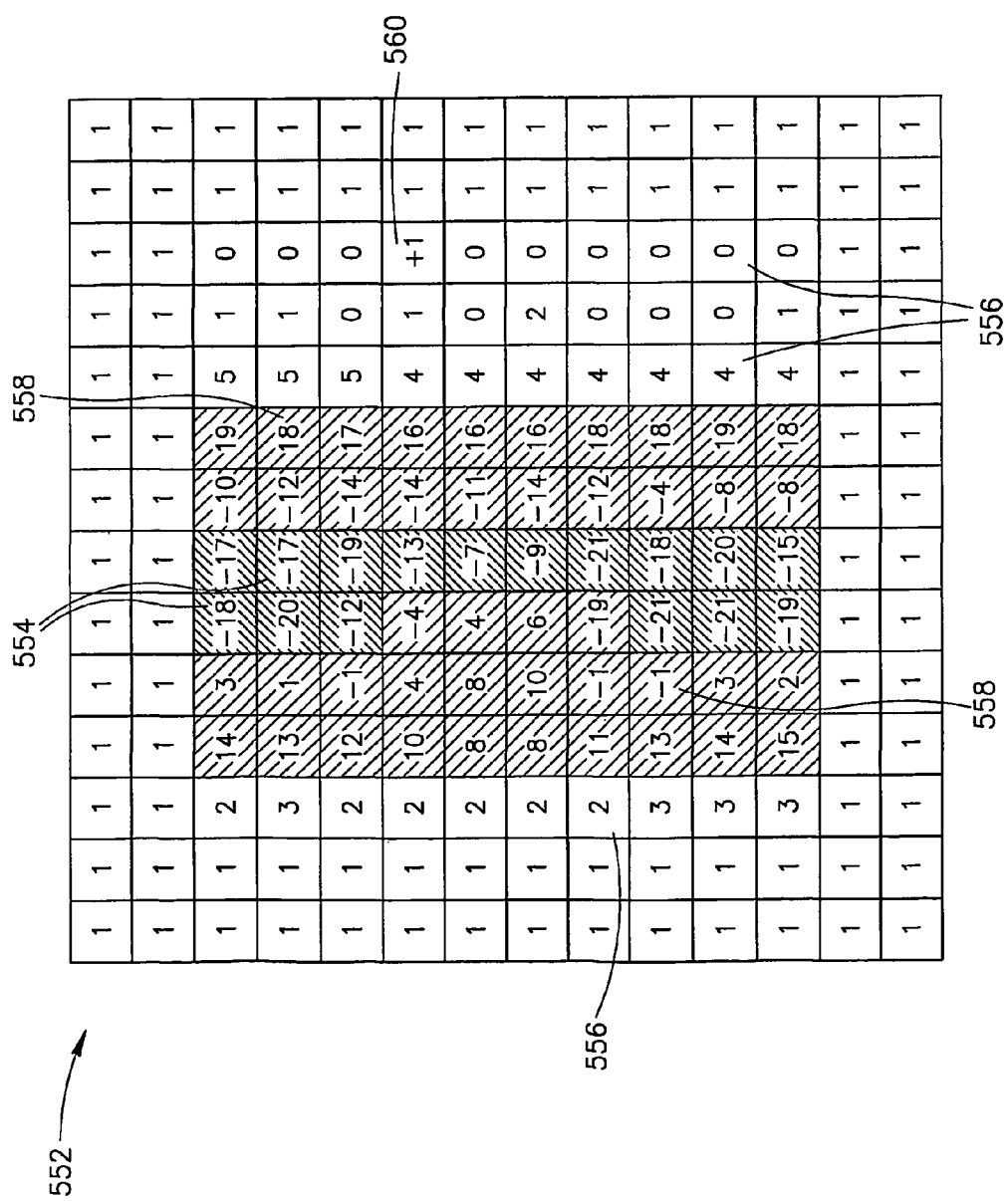
FIG. 8 is the convolved pixel value map of FIG. 7 in which the convolved pixel values are revised to indicate regions of metal conductor and substrate to a high degree of confidence, and other transitional regions.

Reference is now made to FIG. 8, which shows a revised convolved pixel value map 552, which is the convolved pixel value map 452 of FIG. 7 indicating pixels designated as high-sure and low-sure pixels in Block 314. For simplicity of illustration, additional rows and columns along boundaries have been added. High-sure pixels 554 are shown darkly shaded, low-sure pixels 556 are shown without shading, and transitional pixels 558 are shown lightly shaded. In accordance with a preferred method, each high-sure pixel 554 must have a negative convolution value, and each low-sure pixels 556 must have a zero or positive convolution value. If a high-sure pixel 554 contains a positive value, its convolution value is revised to −1. If a low sure pixel 556 contains a negative values, its convolution value is revised to +1. Transitional pixels 558 may contain either positive or negative values and are not revised. The value of pixel 560 for example, has been changed from its initial convolution value of −1 (FIG. 7) to +1 because it is in a low-sure region. Revision of convolution values in view of the high-sure low-sure calculation ensures that extraneous contours do not appear in regions that are known, to a high degree of certainty, to be either copper or laminate. Additionally, the two most extreme pixels on either side of each row and each column, regardless of their type, are modified to ensure that the convolution value is +1, which is representative of substrate.

Block 318: Contour points for putative boundaries between copper conductor 214 and substrate 215 (FIG. 3) are calculated, pixel by pixel, from revised convolved pixel values obtained following Block 316. In accordance with a preferred method, a contour point is deemed to exist at a zero crossing between the center points of a pair of oppositely signed adjacent pixels sharing a side, calculated by linear interpolation based on the respective oppositely signed values of adjacent pixels.

Figure 9:
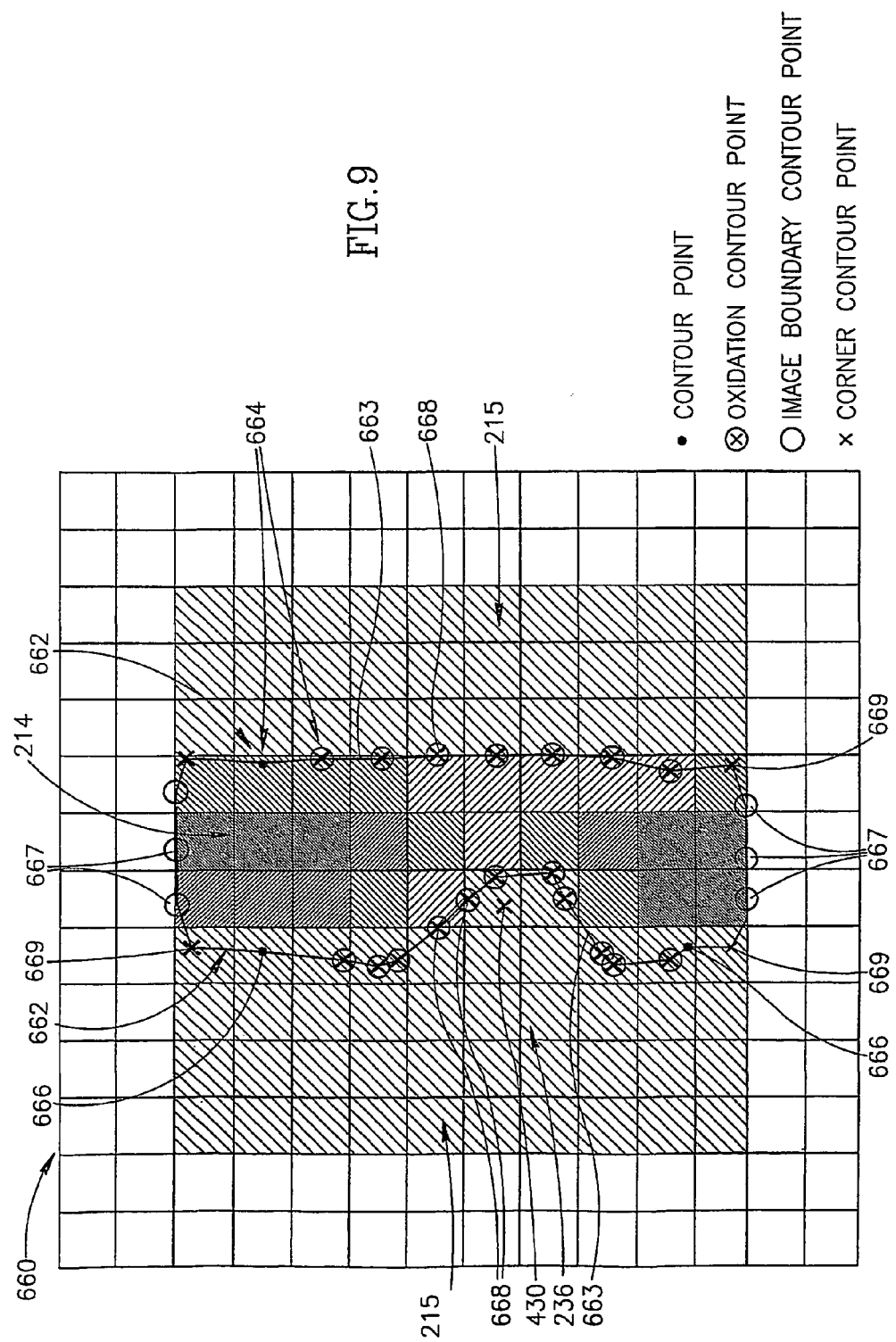
FIG. 9 is a putative contour map showing the approximate location of edges between metal conductor and substrate shown in the image of FIG. 3.

Reference is made to FIG. 9 which shows a putative contour map 660 indicating putative contours 662 between metal conductor 214 and substrate 215 shown in image portion 152 of FIG. 3. Putative contours 662 correspond to a collection of contour elements 663 derived by connecting contour points 664 obtained at block 318, preferably with straight line segments. It is readily appreciated that by designating extreme pixels in each row and column in revised convolved pixel value map 552 (FIG. 8) as being substrate, the putative contour surrounding each conductor 214 is a closed loop.

A candidate defect is determined to be located on or near a conductor if candidate defect indication 430 provided by candidate defect detector 34 is completely surrounded by pixels determined to be copper, or is within a distance of one pixel from a region of pixels determined to be copper.

Preferably, each of the contour points 664 in putative contour map 660 is evaluated and classified as one of (i) a regular contour point, (ii) an image edge contour point, (iii) an oxidation contour point, (iv) a corner contour point, or (v) an oxidation corner based on analysis of red "R", green "G" and blue "B" pixel values contained in snapshot portion 152. Alternatively, contour points are classified into only some of the above types, for example: regular contour points and corner contour points.

In accordance with a preferred method, oxidation contour points, such as oxidation contour points 668, are characterized by a gradient of "R" intensity, with reference to neighboring pixels, that is relatively small, for example only half the average gradient along a contour, while the value of "R" intensity of a oxidation contour point is relatively large compared to the value of the "G" and "B" intensities. The actual and relative gradient and pixel intensity values may be determined empirically.

Therefore, in accordance with a preferred embodiment of the present invention, a contour point 664 is classified as an oxidation contour point 668 if at the contour point either [R'<C1], [R'<C2 and 2R>G+B+C3]. In the equations, the intensity value of a contour point is determined, for example, by bilinear interpolation of four pixels in the vicinity of the contour point, as described, for example, in J. D. Foley et. al., *Computer Graphics: Principles and Practice*, Addison-Wesley, 1990, R' is a normal derivative of the "R" intensity at a contour point 364, and C1, C2 and C3 are constants.

Preferably R' is the first derivative approximation of the R intensity at the contour point 100 along a direction which is outwardly normal to the contour line in which the contour point is located, calculated for a single pixel separation away from the contour point.

In addition, a first contour point 664 is typically classified as an oxidation contour point 668 if it is adjacent to a another contour point 664 that is classified as an oxidation contour point 668 as a result one of the above equations being satisfied at the second contour point 664.

The constants C1, C2 and C3 preferably are empirically determined responsive to imaging parameters that affect "R", "G" and "B" intensities registered by pixels 154 in snapshot portion 152 (FIG. 3). Among these imaging parameters are for example, the spectral sensitivity of a camera used to acquire the source image of the PCB and the spectrum of light used to illuminate the PCB when acquiring the source image.

For example, if "R", "G" and "B" intensities for pixels 154 imaging a PCB are normalized so that for pixels 154 that image substrate 215 R=G=B=0, and for pixels 154 that image copper conductor 214 R=G=B=1. Then, typical values for constants C1, C2, C3 and C4 are C1=0.5, C2=0.6 and C3=0.1. The inventors have found that changes in these values of magnitude less than or equal to about ±0.1 do not substantially affect whether or not a contour point 664 is classified as a regular contour point 666 or an oxidation contour point 668. Under certain circumstances, other values may be chosen.

In FIG. 9, it is seen that putative contour 662 includes contour points that have been classified as regular contour points 666, which are contour points between copper and substrate, image boundary contour points 667, which are contour points formed along an image boundary, oxidation contour points 668 which are contour points that lie on oxidized conductor, and corner contour points 669. Corner contour points are located where putative contour is strongly concave and continues in a changed direction for at least a predetermined extended run of contour points. Determination of a corner may be made by analysis of the triangular region defined within a predetermined distance of pixels from a putative corner. In the vicinity of candidate line width violation defect 236 there are several contiguous oxidation contour points 668, that form a chain of oxidation contour points 664.

Reference is now made to FIG. 10A in which the putative contour map 660 of FIG. 9, a convex hull 680, calculated for oxidation contour points 668 in the vicinity of candidate defect 236, and a directed convex hull 684 are seen.

In accordance with an exemplary embodiment, contour points surrounded by directed convex hull 684, that is contour points that would be on or inside convex hull 680, are evaluated to verify that they are indeed suitable to be representative of copper, for example because they are representative of oxidized copper. Preferably methods of image analysis described with reference to block 330 in FIG. 5A or with reference to FIG. 15 are employed to verify that selected pixels that would be inside the region of convex hull 680 are suitable to be representative of copper, for example oxidized copper. Another preferred method for analyzing the presence of copper includes averaging the "R" "G" and "B" values for the pixels inside the convex hull region, and analyzing whether the averaged value is representative of oxidation based on an adaptation of the method described with reference to block 330. Still another preferred method for verifying whether the region inside the convex hull is representative of oxidized copper is described in Applicant's copending patent application WO 00/11454 referenced above. Any other suitable method for distinguishing oxidized copper from non-oxidized copper may also be used. Typically this analysis is performed only for pixels inside or along a convex hull.

If analysis of pixels corresponding to the region surrounded by directed convex hull 684, namely the region that straddles or that would be inside the convex hull 680, shows that the region is generally not representative of copper or oxidized copper further analysis of the image typically is not necessary because real defect is indicated. Nevertheless, the conductor shape, absent the region inside convex hull 680, typically is measured and if a defect is found the post process reports a real defect for candidate defect 236.

If it is verified from pixel analysis that the region surrounded by directed convex hull 684 is suitable to be representative of copper or oxidized copper, then putative border 662 is modified. Preferably extreme contour points 682 of the convex hull, are determined. An extreme contour point 682 is an oxidation contour point that is bounded by a regular oxidation point 666 or corner oxidation point 669. Putative contour 662 preferably is revised by replacing each contour element 663 extending between extreme contour points 682 with directed hull 684.

Reference is now made to FIG. 10B which corresponds to the same region of conductor 214 as is shown in FIG. 10A, and which illustrates the application of another preferred embodiment for processing contour map 660 and estimating the location of putative border 662 therein, to ascertain the presence or absence of a real defect. As shown in FIG. 10B, inasmuch as candidate defect indication 430 is within a distance of one pixel length from a contour element 663 representing putative contour 662, a directed convex hull 684 is extended between corner contour points 669 which are determined as described hereinabove. Various contour points 664 and pixels 654 that are surrounded by convex hull 684 are evaluated for to ascertain whether they are representative of copper or oxide using any of the suitable methods for evaluating the presence of oxides as described hereinabove. Alternatively, a convex hull 686 may be calculated for all of the contour points 664 between corner contour points 669, and pixels corresponding to the region inside convex hull 686 may be analyzed to determined whether the region inside convex hull 686 is suitable to be representative of copper or oxide.

As seen in FIG. 10B, because contour points 664 and pixels are representative of oxide, computations for determining whether candidate defect 236 is real or specious are conducted on directed convex hull 684, or the region enclosed thereby, as it extends between corner contour points 669.

Once a putative contour 662 is revised in accordance with an edge location approximation represented by directed hull 684, various points along putative contour 662, now including directed convex hull 684, are evaluated to determine whether they are suitable to be representative of copper, or are oxide, using any of the methods described hereinabove. Thus if the region along directed convex hull 684 or enclosed by convex hull 686 is to be considered copper or oxidized copper, preferably, the width of the portion of copper conductor 214 is recalculated now using directed convex hull to represent the approximate location of a contour representing an edge of conductor 214 in putative contour map 660.

Dimension calculation methods are well known. If the width dimension meets predetermined rules applied to an electrical circuit under test, then candidate defect 236 is deemed to be a specious defect, for example resulting from oxidation of the copper conductor. If the width dimension of the portion of copper conductor 214 between contours on both sides of the conductor remains less than a minimum tolerance required by the rules, even after revision of the location of the putative contour, then the defect is attributed to a real absence of copper, candidate defect 246 is deemed to be a real line width violation and a real defect report is generated.

Figure 11:
FIG. 11 is a portion of a snapshot image corresponding to a pixel neighborhood surrounding a second candidate line width defect visible in FIG. 2.

Reference is now made to FIG. 11 which is a portion 752 of snapshot 52 corresponding to the pixel neighborhood immediately surrounding candidate major line width violation 738 corresponding to major line width violation 38 seen in FIG. 2. Candidate line width violation is a real line width violation resulting from a real absence of copper in conductor portion 714, and not merely oxidation of a part of the conductor.

Figure 12A:
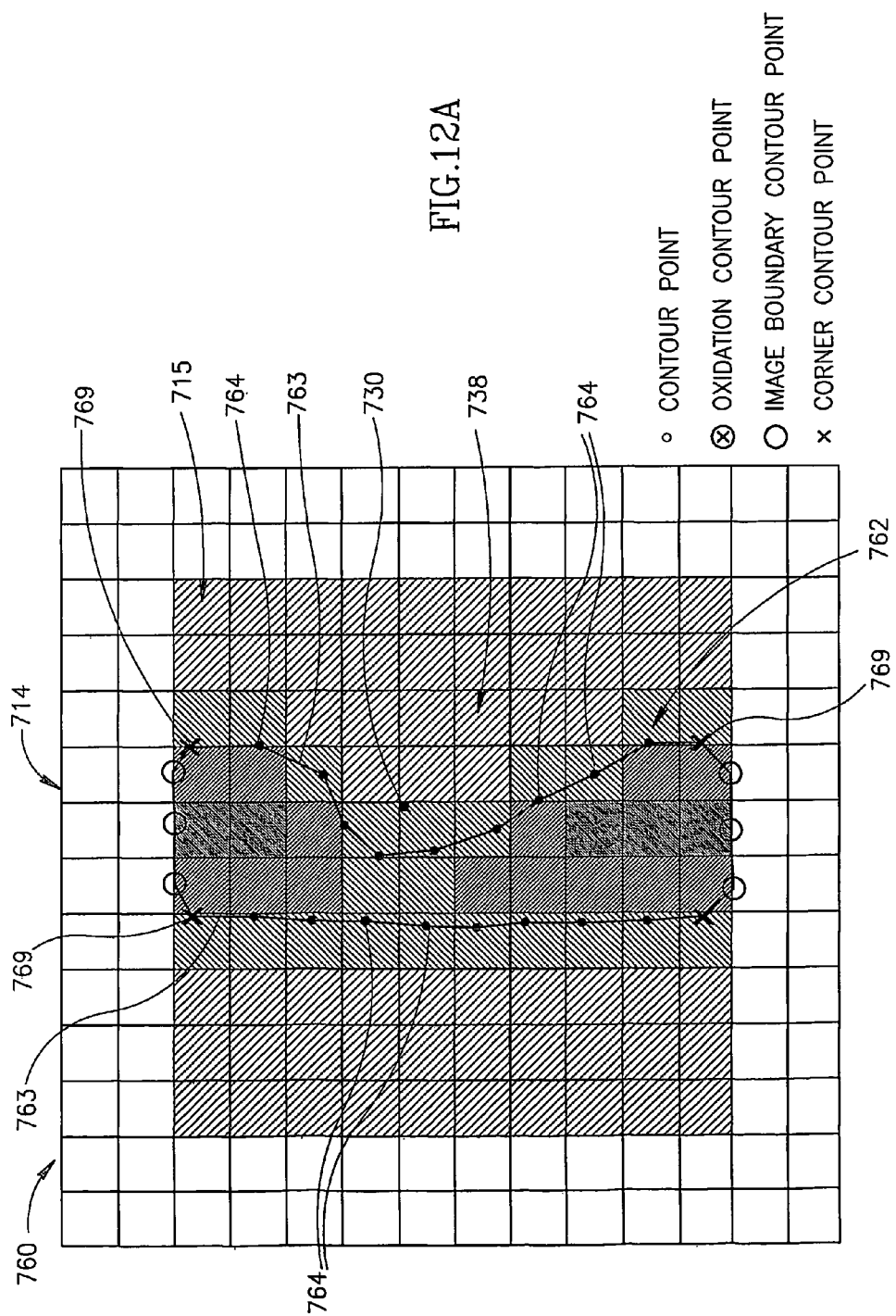
FIG. 12A is a putative contour map which indicates putative boundaries between metal conductor and substrate shown in the image of FIG. 11.

Reference is additionally made to FIG. 12A which shows a contour map 760 generated at block 310 (FIG. 5A) for image portion 752, and illustrates the application of a preferred method for processing contour map 760 to ascertain the presence or absence of a real defect. Inasmuch as candidate defect indication 730 is within a distance of one pixel length from a contour element 763 representing putative contour 762, contour points 764 along contour 762 are evaluated to determine their type, namely regular contour point 766, corner contour point 769, or oxidized contour point (not present in contour map 760). Thus, evaluation of "R", "G" and "B" pixel values shown in FIG. 11 shows that oxidation is not present at any of contour points 764, each of which is designated as regular contour points 766. Because none of contour points 764 are oxidation contour points, there is no need to calculate a convex hull. The width of conductor 714 is computed without revising putative contour 762 and in the example of FIG. 12A, a real defect report is issued for candidate defect 738.

Figure 12B:
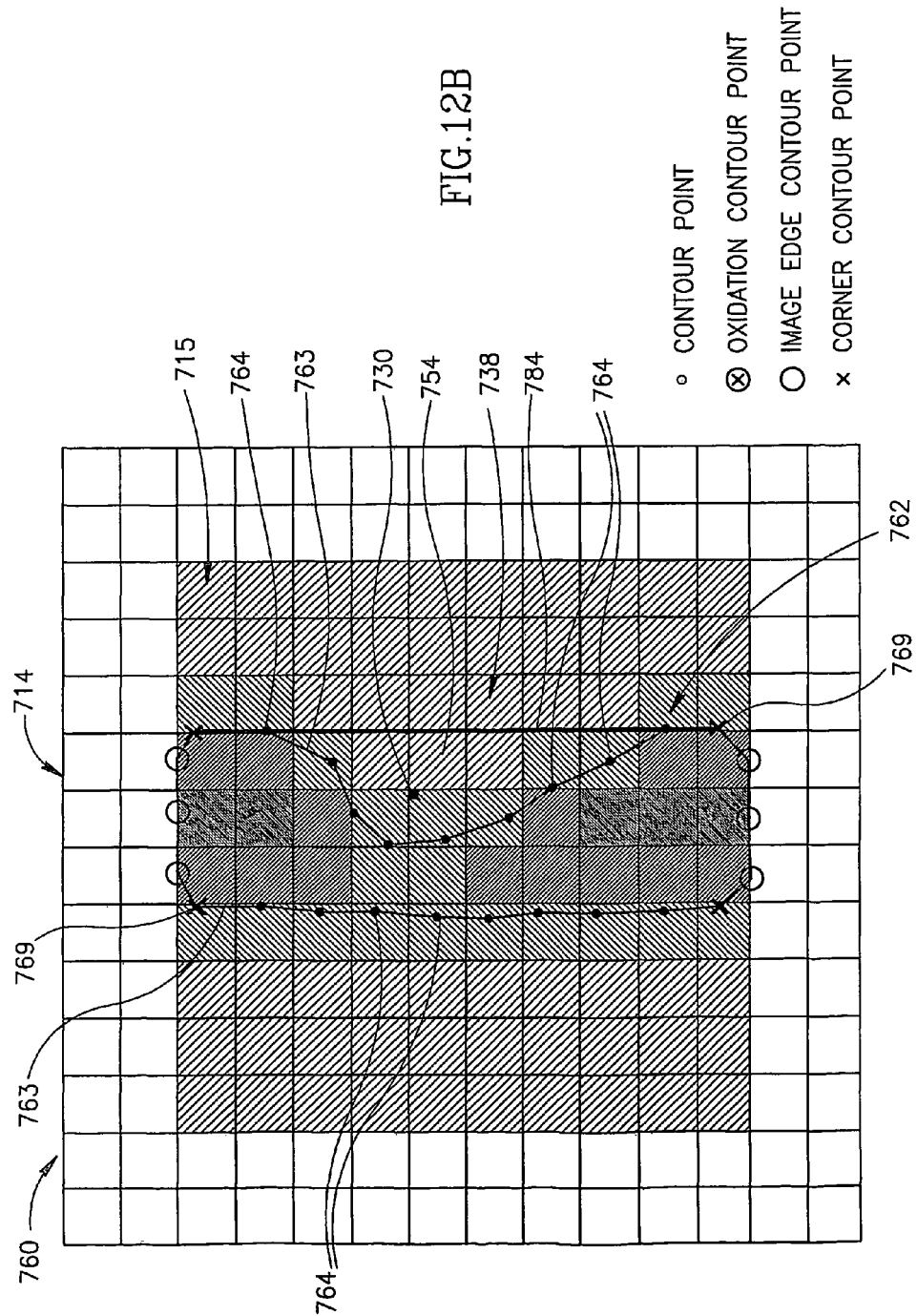
FIG. 12B is a putative contour map which indicates putative boundaries between metal conductor and substrate shown in the image of FIG. 11 and a directed convex hull in accordance with an exemplary method of the invention.

Reference is additionally made to FIG. 12B which shows a contour map 760 generated at block 310 (FIG. 5A) for image portion 752, and illustrates the application of another preferred method for processing contour map 760, and estimating the location of putative contours 762 therein, to ascertain the presence or absence of a real defect. As seen in FIG. 12B, inasmuch as candidate defect indication 730 is within a distance of one pixel length from a contour element 763 representing putative contour 762, a directed convex hull 784 is extended between corner contour points 769. Various contour points 764 and pixels 754 which are surrounded by directed convex hull 784 are evaluated for the presence of oxides, or to determine whether the region adjacent to directed convex hull 784 is suitable to be considered copper, using any of the suitable methods for evaluating the presence of copper and oxides as described hereinabove. Because none of contour points 764 or pixels 754 exhibit oxidation, the width of conductor 714 is computed without revising putative contour 762 and in the example of FIG. 12B, a real defect report is issued for candidate defect 738.

Figure 13:
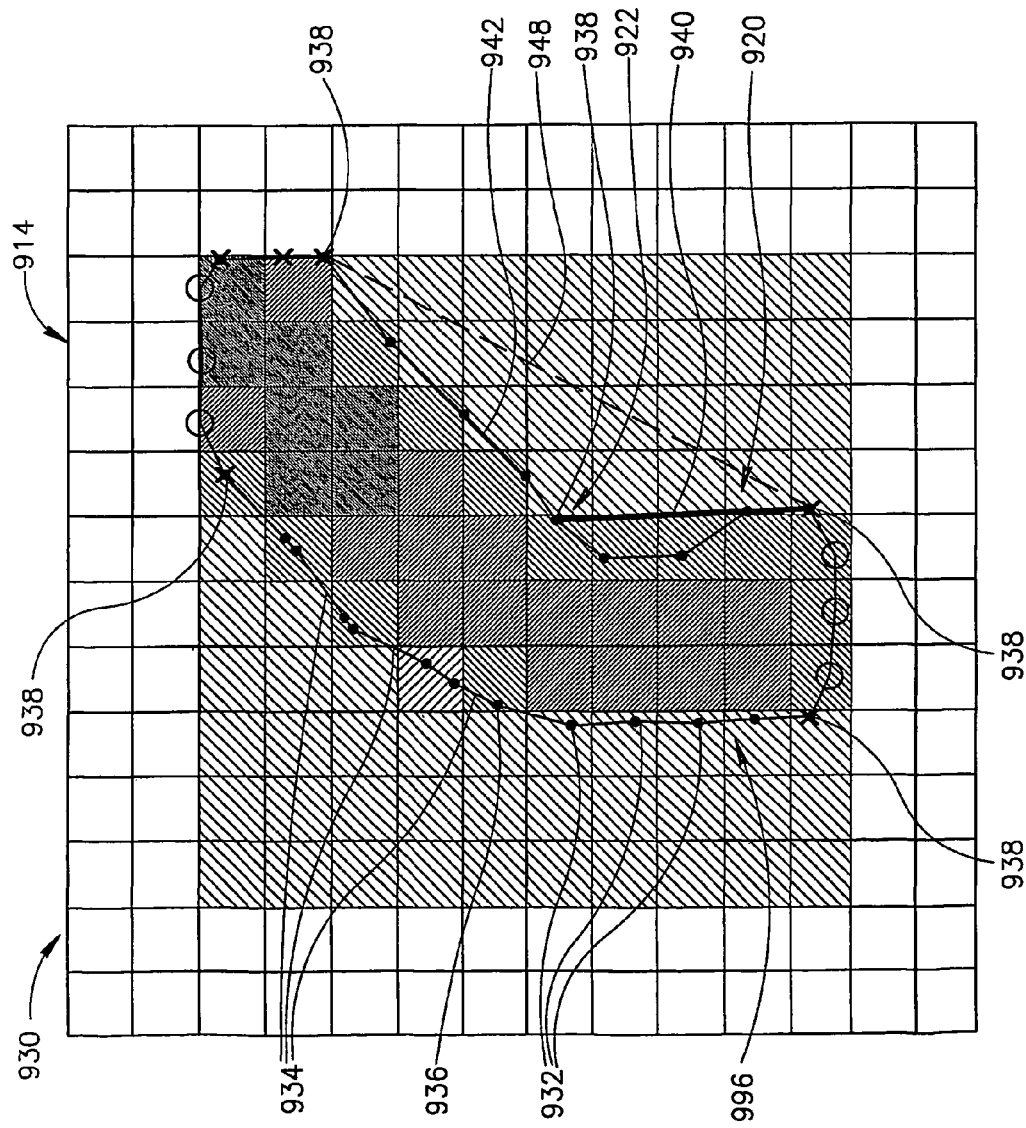
FIG. 13 shows a putative contour map which indicates putative boundaries between metal conductor and substrate for a suspected corner defect, and a directed convex hull in accordance with an exemplary method of the invention.

Reference is now made to FIG. 13 which is a contour map illustrating contours for the portion of a conductor 914 in the region of a corner candidate defect 920, corresponding to candidate defect 46 in FIG. 2.

In accordance with a preferred embodiment of the present invention, a contour map 930 indicating the location of contour points 932 and contour elements 934, which define putative contours 936 for conductor 914 is preferably created from a full color image using the methods described in detailed hereinabove. Contour points 932 are identified, and corner contour points 938 are detected. Contour points may be classified as regular contour points, oxidized contour points, image edge contour points, corner contour points, corner oxidation contour points as described hereinabove. It is noted that a corner contour point corresponding to corner 44 (FIG. 2) is located along putative contour 936.

Preferably, directed convex hulls, such as directed convex hulls 940 and 942, are calculated for each section of putative contour 936 that extends between sequential corner contour points 938 in the vicinity of candidate defect 920. Preferably, directed convex hulls are calculated for sequential corner contour points 938 to avoid inclusion of regions that are not part of conductor 914, such as region 944 defined by aberrant hull 946. Various contour points 932 or pixels 948 surrounded by directed convex hulls 940 and 942 are evaluated as to whether they are representative of copper or oxide as described hereinabove. Thus, if copper or oxide is detected the width of conductor 914 preferably is recalculated with reference to a modified putative contour at least partially formed convex hulls 940 and 942, and an appropriate real or specious defect report is made; if oxides are not detected, then putative contours are not revised.

The present invention has been described using non-limiting detailed descriptions of preferred embodiments thereof that are provided by way of example and are not intended to limit the scope of the invention. Variations of embodiments described will occur to persons of the art, and the methods described herein may be applied to various putative defects in electrical circuit inspection.

The scope of the invention is limited only by the following claims. In the claims and description of the present application, "comprise" "include" and "have", and conjugates thereof, mean "including, but not necessarily limited to."

The invention claimed is:

1. A method for automatically optically inspecting an electrical circuit, comprising:
acquiring at least one non-binary optical image of an electrical circuit;
generating at least one binary first inspection image from the at least one non-binary optical image and processing said binary first inspection image to determine therefrom regions of candidate defects in the electrical circuit;
generating at least one additional inspection image, from said at least one non-binary optical image, for regions surrounding candidate defects, said at least one additional inspection image at least partially including information for an optical characteristic that is not included in the at least one binary first inspection image; and
determining whether the candidate defect is a specious defect by inspecting the at least one additional inspection image.

2. A method according to claim 1 wherein acquiring includes acquiring a polychromatic image of the electrical circuit.

3. A method according to claim 2 wherein the polychromatic image comprises a red, a green and a blue component.

4. A method according to claim 3 wherein the additional inspection image comprises each of the red, green and blue components acquired in the polychromatic image.

5. A method according to claim 1 wherein the binary first inspection image is derived only from a red color component of the acquired image.

6. A method according to claim 1 and wherein the at least one binary first inspection image includes a monochromatic gray level representation of the electrical circuit.

7. A method according to claim 6 wherein the monochromatic gray level representation is derived only from a red color component of the acquired image.

8. A method according to claim 1 and wherein the binary first inspection image and the additional inspection image are derived from the same optical image.

9. A method according to claim 1 and wherein the candidate defects are determined automatically.

10. A method according to claim 1 and wherein the actual defects are determined automatically.

11. A method of inspecting an electrical circuit, comprising:
acquiring a non-binary image of an electrical circuit;
processing said non-binary image to derive a binary representation of said electrical circuit;
determining the presence of a candidate defect in the electrical circuit at least in part from analyzing the binary representation;
defining a portion of said non-binary image corresponding to a region surrounding said candidate defect; and
determining the presence of an actual defect in the electrical circuit from analyzing said portion of the non-binary image.

12. A method according to claim 11 wherein the binary representation covers a larger extent of the circuit than said portion of the non-binary image.

13. A method according to claim 11 including:
providing a gray level monochrome representation of the circuit, and
determining candidate defects in the electrical circuit at least in part by analyzing both the binary representation and the gray level monochrome representation.

14. A method according to claim 13 and including identifying real defects from analyzing the binary representation and the gray level monochrome representation.

15. A method according to claim 11 wherein defects determined utilizing said binary image include actual defects and wherein said actual defects include one or more of: missing features in an electrical circuit, misplaced features in an electrical circuit, extraneous features in an electrical circuit, pinholes and scratches.

16. A method according to claim 11 wherein the binary representation is prepared to a resolution which is finer than an optical resolution of the non-binary image from which it is derived.

17. A method according to claim 11 wherein candidate defects comprise suspected shape aberration in a metal conductor in the electrical circuit.

18. A method according to claim 17 wherein in an optical image of the electrical circuit metalized portions in the electrical circuit have a first optical characteristic, non-metalized portions have a second optical characteristic, and regions of suspected shape aberration have a third optical characteristic which is different from the optical characteristics of the metalized portions and the non-metalized portions.

19. A method according to claim 18 wherein the optical characteristic comprises intensity of reflectance.

20. A method according to claim 18 wherein the optical characteristic comprises color.

21. A method claim 11 wherein processing said non-binary image comprises selecting a gray level image from a single channel of a multichannel polychromatic image of the electrical circuit.

22. A method according to claim 11 wherein the non-binary image is a polychromatic image of the electrical circuit.

23. Apparatus for automatically optically inspecting electrical circuits, comprising:
   at least one optical sensor operative to acquire a non-binary image of an electrical circuit;
   a first image processor operative to generate a binary representation of the electrical circuit from the non-binary image and to analyze said binary representation to determine therefrom suspected defects in the electrical circuit;
   a snapshot generator operative to receive said non-binary image from the at least one optical sensor, and reports of suspected defects from the first image processor, and to generate non-binary neighborhood images defining regions surrounding suspected defects; and
   an image post processor operative to analyze the non-binary neighborhood images and to determine therefrom the presence of real defects.

24. Apparatus according to claim 23 wherein the first image processor generates a first representation which is a binary representation of the electrical circuit.

25. Apparatus according to claim 24 wherein the optical sensor has an optical resolution and the binary representation of the electrical circuit is generated a resolution that is finer than the optical resolution.

26. Apparatus according to claim 23 wherein, suspected defects comprise false defects and real defects, and the image post processor is operative to analyze said neighborhood images to distinguish false defects from real defects.

27. Apparatus according to claim 24 additionally comprising a gray level image processor, wherein at least some anomalies detected by the gray level image processor are real defects and at least some anomalies detected by the binary image processor are false defects.

28. Apparatus according to claim 23 wherein said neighborhood images are polychromatic images.

29. Apparatus for automatically optically inspecting electrical circuits according to claim 28 and wherein the polychromatic images are color images.

* * * * *